(12) United States Patent
Chiang et al.

(10) Patent No.: US 11,208,699 B2
(45) Date of Patent: Dec. 28, 2021

(54) EPSTEIN-BARR VIRUS VARIANTS

(71) Applicant: The University of Hong Kong, Hong Kong (CN)

(72) Inventors: Alan Kwok Shing Chiang, Hong Kong (CN); Kwai Fung Hui, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 16/670,856

(22) Filed: Oct. 31, 2019

(65) Prior Publication Data

US 2020/0140961 A1    May 7, 2020

Related U.S. Application Data

(60) Provisional application No. 62/755,201, filed on Nov. 2, 2018.

(51) Int. Cl.
| | | |
|---|---|---|
| *C12Q 1/6888* | (2018.01) | |
| *C12Q 1/70* | (2006.01) | |
| *C12Q 1/686* | (2018.01) | |

(52) U.S. Cl.
CPC .......... *C12Q 1/6888* (2013.01); *C12Q 1/686* (2013.01); *C12Q 1/70* (2013.01); *C12Q 2535/131* (2013.01); *G01N 2800/50* (2013.01); *G01N 2800/7028* (2013.01)

(58) Field of Classification Search
None
See application file for complete search history.

(56) References Cited

PUBLICATIONS

Tsao et al. Epstein-Barr virus infection and nasopharyngeal carcinoma. Phil. Trans. R. Soc.; 2017; B 372: 20160270, p. 1-15. (Year : 2017).*
Palser et al., Genome Diversity of Epstein-Barr Virus from Multiple Tumor Types and Normal Infection. Journal of Virology; 2015; 89: 5222-5237. (Year: 2015).*
Kwok et al. Genomic Sequencing and Comparative Analysis of Epstein-Barr Virus Genome Isolated from Primary .Nasopharyngeal Carcinoma Biopsy. PLOS ONE; 2012; 7; 5; e36939: p. 1-10. (Year: 2012).*
Supplemental Tables S1 and S2, Kwok et al. Genomic Sequencing and Comparative Analysis of Epstein-Barr Virus Genome Isolated from Primary .Nasopharyngeal Carcinoma Biopsy. PLOS ONE; 2012; 7; 5; e36939: p. 1-10. (Year: 2012).*
Zeng, et al. Genomic sequence analysis of Epstein-Barr virus strain GD1 from a nasopharyngeal carcinoma patient. J Virol; 2005; 79: 15323-15330. (Year: 2005).*
Chen et al. Nasopharyngeal Epstein-Barr Virus Load: An Efficient Supplementary Method for Population-Based Nasopharyngeal Carcinoma Screening. PLOS ONE; 2015; 1-13. (Year: 2015).*
Kwok et al., PLOS ONE; 2012; 7; 5; e36939: p. 1-10. (Year: 2012).*
Kwok et al., PLOS ONE; 2012; 7; 5; e36939: p. 1-10. Supplemental information. (Year: 2012).*
Palser et al. Journal of Virology; 2015; 89: 5222-5237. (Year: 2015).*
Tsao et al. Epstein-Barr virus infection and nasopharyngeal carcinoma (Review).P hil. Trans. R. Soc.; 2017; B 372: 20160270, p. 1-15 (Year: 2017).*

* cited by examiner

*Primary Examiner* — Juliet C Switzer
*Assistant Examiner* — Wahwah T Johnson
(74) *Attorney, Agent, or Firm* — Kilpatrick Townsend & Stockton LLP

(57) ABSTRACT

The present invention provides novel Epstein Barr virus (EBV) variants including those associated with increased risk for developing nasopharyngeal carcinoma (NPC).

10 Claims, 13 Drawing Sheets
(11 of 13 Drawing Sheet(s) Filed in Color)

Figure 1A
Figure 1B
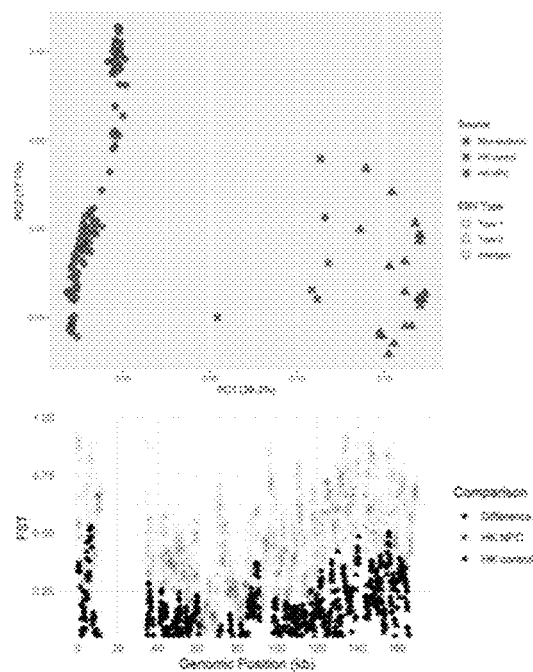
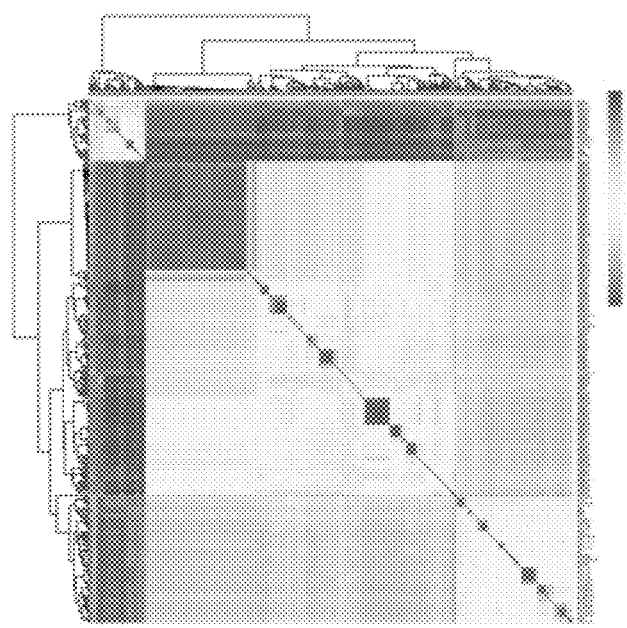
Figure 1C

Figure 2A
Figure 2B
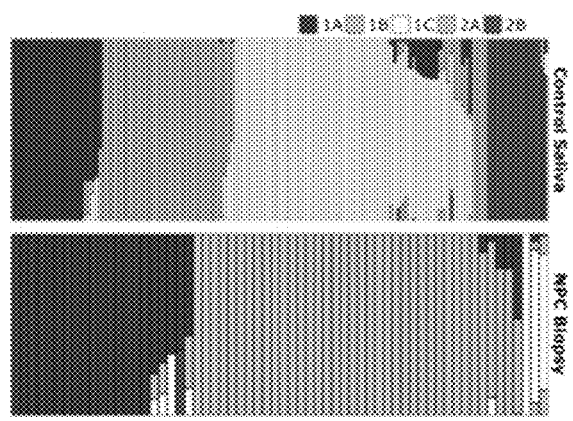
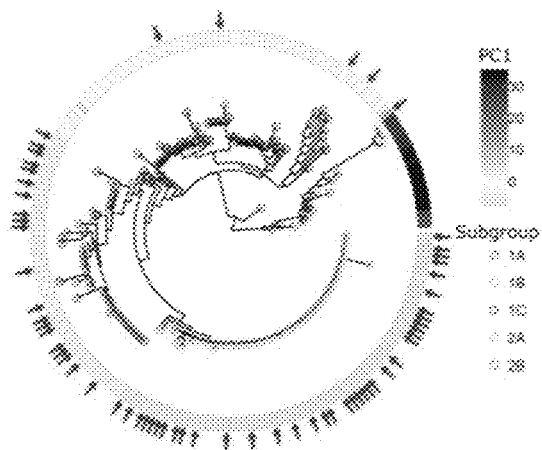
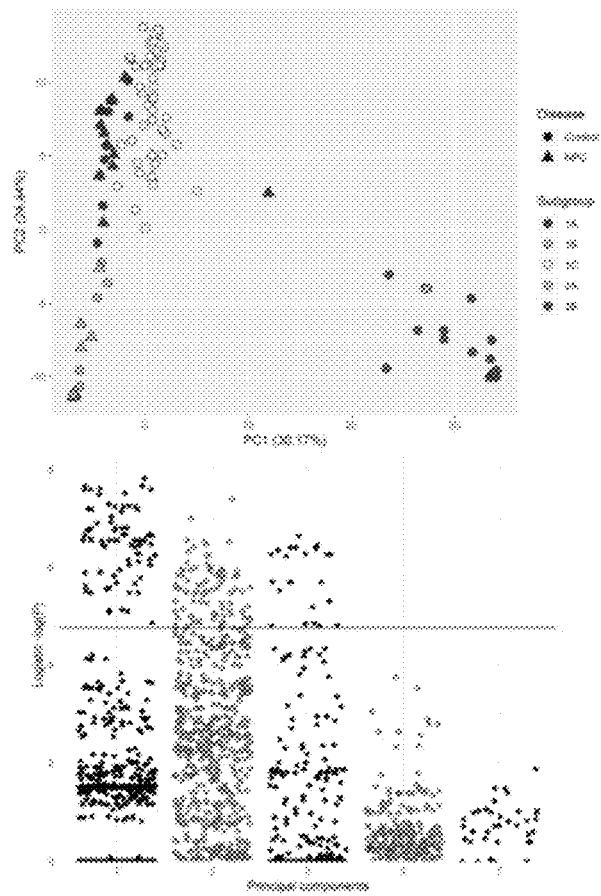
Figure 2C
Figure 2D

Figure 3A
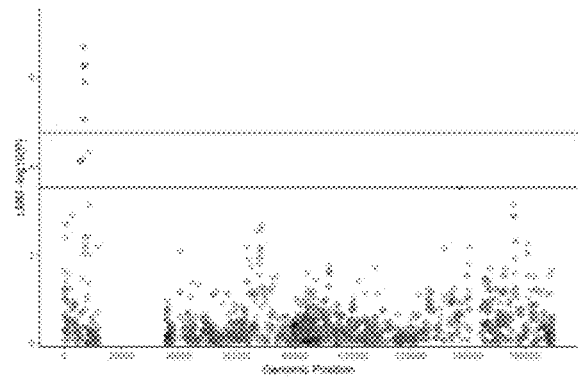
Figure 3B
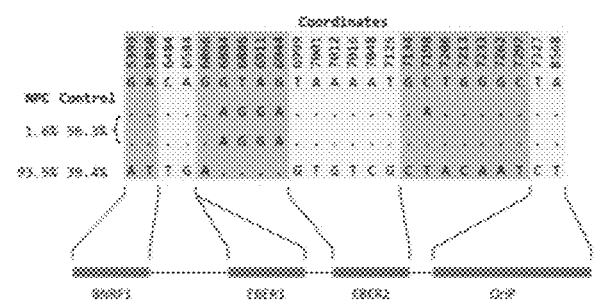
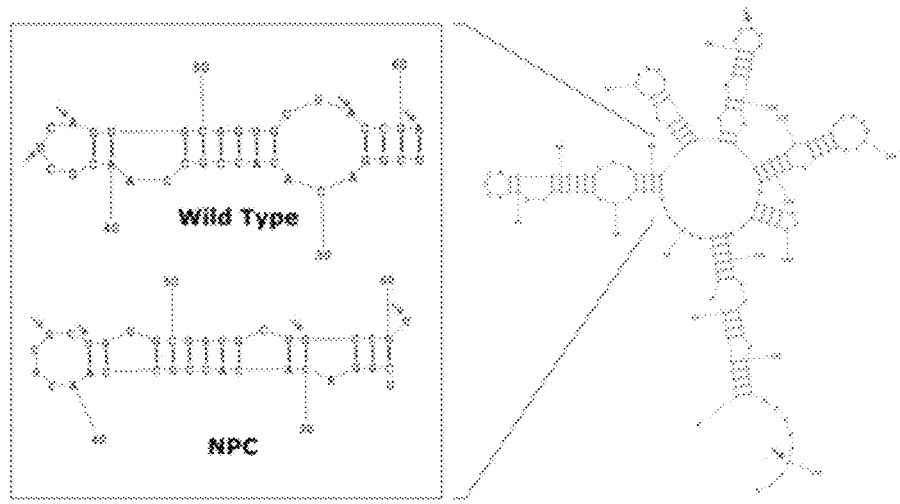
Figure 3C

Figure 4A
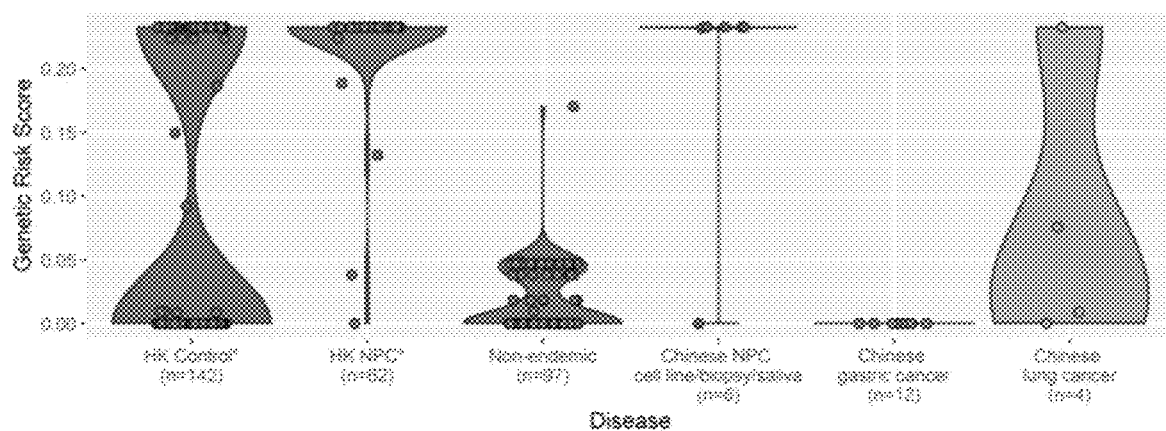
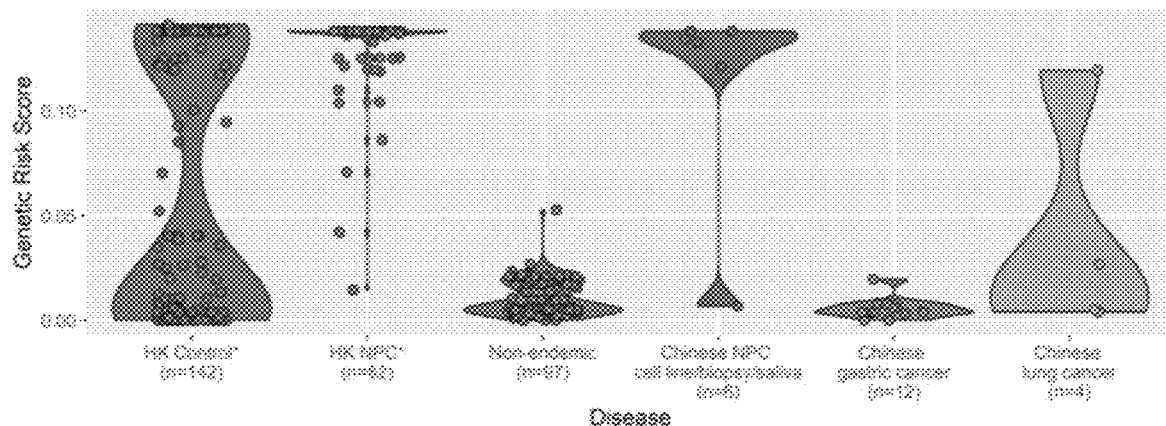
Figure 4B

EPSTEIN-BARR VIRUS VARIANTS

This application claims priority to U.S. Provisional Patent Application No. 62/755,201, filed Nov. 2, 2018, the contents of which are hereby incorporated by reference in the entirety for all purposes.

BACKGROUND

Nasopharynx cancer or nasopharyngeal carcinoma (NPC) is the most common cancer originating in the nasopharynx. Globally NPC deaths are numbered at about 70,000 each year. Seen primarily in middle-aged patients, NPC can also afflict children. While it is uncommon in the United States and most other nations with an incidence of less than 1 case in 100,000 people, NPC accounts for 18% of all cancers in China, being extremely common in southern regions of China, particularly in Guangdong Province. It is sometimes referred to as Cantonese cancer because its incidence is at about 25 cases per 100,000 people in this region, 25 times higher than the rest of the world. This disease is also quite common in Taiwan. Although the precise cause of increased risk for NPC in these regions is yet to be illustrated, viral, dietary, and genetic factors have been implicated in its causation. For example, the South East Asian diet including consumption of significant quantity of salted vegetables, fish and meat is thought to contribute this disease. The viral risk of NPC is associated with Epstein-Barr virus (EBV) infection. EBV is one of the most common viruses, with 95% of all people in the U.S. exposed to this virus by the time they are in their 30 s or 40 s.

Like other viruses, EBV are known to have many variants. Whether certain variants of EBV are linked to the pathogenesis of NPC, which shows a marked geographic restriction, remains an unresolved question. Because of the prevalence of NPC and its severe social and economical impact, there exists an urgent need for new and more effective methods for the early diagnosis or risk assessment of NPC in individuals, especially those living in the high risk geographic areas. This invention fulfills this and other related needs.

SUMMARY OF THE INVENTION

The present inventors performed a case-control study comparing genomic sequences of EBV isolated from saliva samples of 142 population carriers with those from primary tumour biopsies derived from 62 patients with NPC of Hong Kong. Cluster analysis discovered five EBV subgroups 1A-C and 2A-B amongst the population carriers in contrast to the predominance of 1A and -B in the majority (95.2%) of NPC. Genome-wide association study (GWAS) identified a panel of single nucleotide polymorphisms (SNPs) and indels associated with NPC, with the most significant SNPs and indels located in the EBER locus. Predicted secondary structure of EBER2 is altered with likely functional consequence in nearly all NPC cases. Using the SNPs associated with NPC, genetic risk score is assigned for each EBV variant. EBV variants with high genetic risk score are found to be much more prevalent in Hong Kong Chinese than individuals of other geographic regions and in NPC than other EBV-associated cancers. It is thus concluded that high risk EBV variants with defined genomic characteristics are strongly associated with NPC.

In the first aspect, the present invention describes novel risk alleles (such as certain SNPs and indels) in EBV genomic sequence associated with NPC and therefore provides a method for assessing the risk of NPC or diagnosing NPC in an individual by detecting in a biological sample taken from the individual EBV variants comprising at least one preferably more of such SNPs. The method includes these steps: (i) performing an assay to determine polynucleotide sequence of at least a portion of EBV genomic sequence present in a biological sample taken from the individual; (ii) detecting one or more risk alleles (including SNPs and indels) in Table 1 or Table 2; and (iii) determining the individual as having an increased risk of developing NPC.

In some embodiments, the method further includes, prior to step (i), a step of isolating DNA from the sample. In some embodiments, the method further includes, prior to step (i), a step of performing an amplification reaction, such as a polymerase chain reaction (PCR), to amplify at least a portion of EBV genomic sequence. In some embodiments, the sample is a saliva sample. In some embodiments, the sample is a such as a swab sample containing nasopharyngeal epithelial cells.

In some embodiments, the assay in step (i) comprises a sequencing assay, such as next generation sequencing, sanger sequencing, sequence-specific PCR or polynucleotide hybridization assay. In some embodiments, two or more risk alleles (including SNPs and indels) in Table 1 or Table 2 are detected in step (ii). In some embodiments, the one risk allele is selected from Table 1, such as 5399A, 5850T, 6484T, 6584G, 7125G, 7134C, 7187A, 7198T, 7206A, 7213C, 7233A, 7262A, 7297T, 7327C, 8568T, 137316C, 59515CCTCCTT, and 59518CCTCCTA, especially 7187A. In some embodiments, the two or more risk alleles are independently selected from 5399A, 5850T, 6484T, 6584G, 7125G, 7134C, 7187A, 7198T, 7206A, 7213C, 7233A, 7262A, 7297T, 7327C, 8568T, 137316C, 59515CCTCCTT, and 59518CCTCCTA, or 7187A along with another risk allele set forth in Table 1.

In some embodiments, the individual being tested by the claimed method is a human subject residing in the South East Asia, such as Hong Kong or Guangdong Province of China. In some embodiments, the individual is a Chinese, who may be a man, a woman, or a child younger than 18 years of age. In some embodiments, the individual has not clinical symptoms of NPC, whereas in other cases, the individual may exhibit some early symptoms of NPC. In some embodiments, upon determination that the individual being tested has an elevated risk of later developing NPC, the method further includes a step (iv) of a therapeutic or prophylactic measure to address the risk of NPC, such as eliminating salted foods from the individual's diet and/or following a continued monitoring scheme for early detection of NPC symptoms, including the necessary physical examination scheduled at a regular frequency such as yearly, semi-yearly frequency. One exemplary diagnostic technique useful for this purpose is nasopharyngoscopy, a procedure that allows the internal surfaces of the nose and throat to be examined with a fibre-optic instrument, which can be performed on a regular basis by a physician on a patient, who is selected after the patient has been determined by the methods described above and herein as an individual having an elevated risk of later developing NPC.

In a second aspect, the present invention provides a kit for assessing risk of developing NPC or detecting NPC in an individual. The kit comprises a first container containing a reagent for detecting a first risk allele (such as a SNP or an indel) of EBV genomic sequence and a second container containing a reagent for detecting a second risk allele (such as a SNP or an indel) of EBV genomic sequence, wherein the first and second risk alleles are independently selected from Table 1 or Table 2.

In some embodiments, the first and second risk alleles are independently selected from Table 1, such as 5399A, 5850T, 6484T, 6584G, 7125G, 7134C, 7187A, 7198T, 7206A, 7213C, 7233A, 7262A, 7297T, 7327C, 8568T, 137316C, 59515CCTCCTT, and 59518CCTCCTA, or 7187A along with another risk allele set forth in Table 1. In some embodiments, the kit further comprises one or more reagents for an amplification reaction, such as PCR, of at least a portion of EBV genomic sequence. In some embodiments, the one or more reagents comprise a set of oligonucleotide primers for PCR. In some embodiments, the kit further comprises user instructions for using the kit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C Geographic differences between EBV variants isolated from individuals of Hong Kong and non-endemic regions. (FIG. 1A) Principal component analysis of EBV genomes isolated from 142 healthy carriers and 62 NPC patients of Hong Kong and 97 individuals of non-endemic regions. Percentages of variance explained are indicated in the axes. (FIG. 1B) Hierarchical clustering of pairwise distance amongst EBV genomes. The figure displays a sample by sample matrix where the distances are represented in colour scales from red (distant) to blue (close). The sources of the samples are indicated at the top of each column with the same colour codes used in FIG. 1a. (FIG. 1C) Fixation index ($F_{ST}$) with respect to non-endemic EBV along the genome amongst type 1 EBV. Each dot represent the $F_{ST}$ in 1000 nucleotide region comparing type 1 Hong Kong NPC (HK NPC; red) or controls (HK control; blue) with type 1 non-endemic EBV. The difference (black) between the two $F_{ST}$ values in each region is shown.

FIGS. 2A-2D Population structure of EBV variants isolated from population carriers and NPC patients of Hong Kong. (FIG. 2D) Admixture analysis output from Bayesian Analysis of Population structure (BAPS).[2-4] Each sample is represented by a column split into up five colours. Each colour represents a subgroup and the length shows the percentage of the ancestral source in an assembly. (FIG. 2B) Principal component analysis of 142 Hong Kong controls and 62 NPC samples. Percentages of variance explained are indicated in the axes. The PCs on the x-axis is sorted by their significance. (FIG. 2C) Maximum likelihood phylogenetic tree of the total 204 samples. Red arrow points to NPC cases. The colour intensities of the outer ring represent the values of samples in PC1. (FIG. 2D) The association tests for SNPs under logistic regression model adjusting for sex and age. The PCs on the x-axis are order by their significance to NPC. Only the top 5 PCs are shown. The red lines show the genome-wide significance cut-off.

FIGS. 3A-3C Identification of the strongest NPC-associated SNPs in the EBER region by GWAS. (FIG. 3A) Manhattan plot from the GWAS. The results are based on 2850 SNPs with MAF>0.05 in a dataset of EBV derived from 62 biopsies of NPC patients and 142 saliva samples of controls. The red line shows the genome-wide cut-off $p=1.75\times10^{-5}$ after Bonferroni correction. The blue line shows the cut-off when controlling false discovery rate at 0.05. (FIG. 3B) Three major haplotypes of SNPs near EBERs (refer to Table 1) in NPC cases and controls. Dots represent reference genotypes. Rare haplotypes, which are found in only 1 sample, are not shown. (FIG. 3C) Predicted RNA secondary structures of EBER2 wild-type and the mutant commonly found in NPC cases. Left, the stem loop that is structurally different between wild type and NPC dominant EBER2. Right, the predicted RNA secondary structure of EBER2. Red arrows denote the significant SNPs identified in GWAS.

FIGS. 4A-4B Genetic risk scores (GRS) of EBV variants isolated from different types of samples and geographic regions. The GRS is calculated based on the SNPs in (FIG. 4A) EBER locus and (FIG. 4B) EBER locus+PC1 SNPs that are significant in logistic regression model (refer to Table 1 and Table 2). The distributions of GRS are shown with violin plots. The width represents the density of points. The maximum widths are normalised across categories for clarity. *data used in GWAS.

DEFINITIONS

Figure 5:
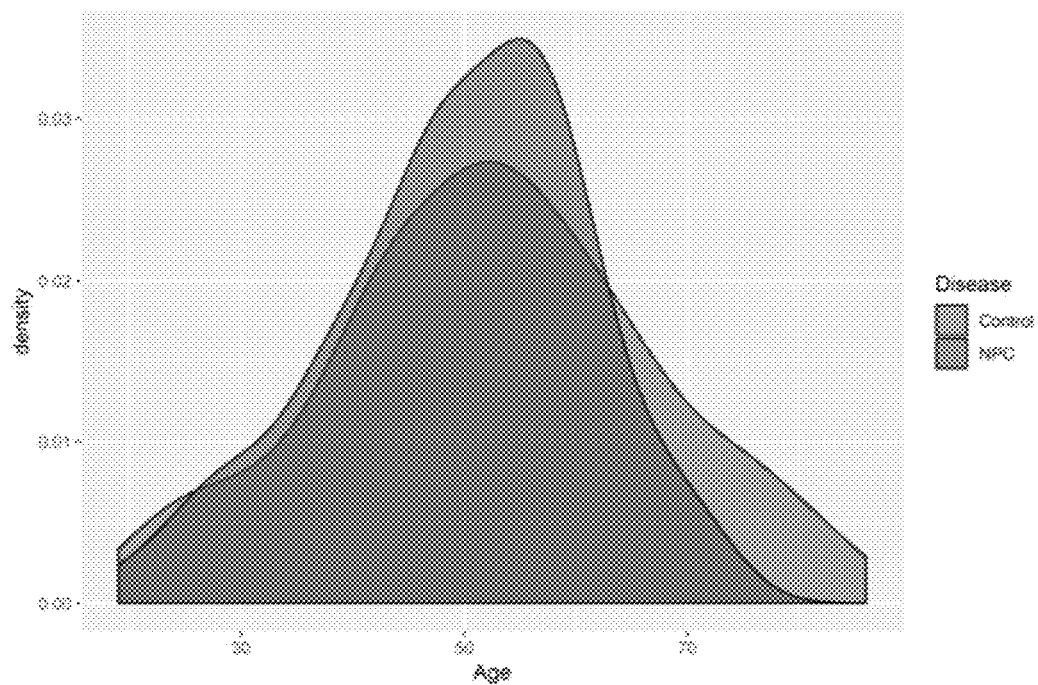
FIG. 5 The distribution of age (upper) and gender (lower) in the dataset.
Figure 5:
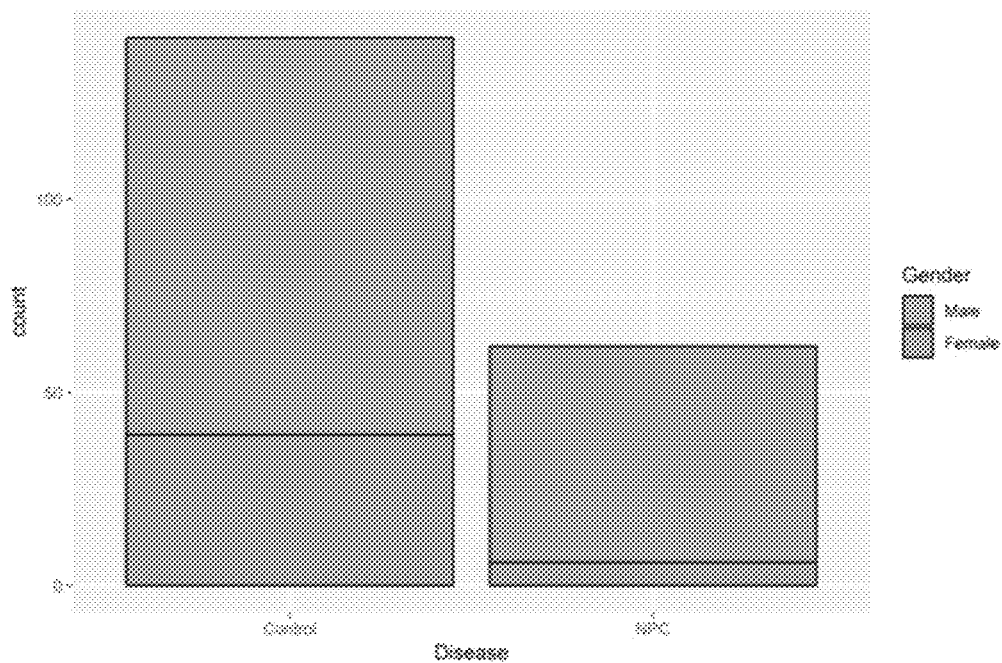

The Epstein-Barr virus (EBV), also called human herpesvirus 4 (HHV-4), one of the most common viruses in humans, is among eight known human herpesvirus types in the herpes family. A double-strained deoxyribonucleic acid (DNA) virus containing about 172,000 base pairs and 85 genes, EBV is best known as the cause of infectious mononucleosis ("mono" or "glandular fever"). Its transmission is by oral transfer of saliva or genital secretions. EBV infects B cells of the immune system and epithelial cells. Once EBV's initial lytic infection is brought under control, EBV latency persists in the individual's B cells for the rest of the individual's life. EBV is also associated with various types of cancer, such as Hodgkin's lymphoma, Burkitt's lymphoma, gastric cancer, nasopharyngeal carcinoma, and conditions associated with human immunodeficiency virus, such as hairy leukoplakia and central nervous system lymphomas. About 200,000 cancer cases per year are thought to be attributable to EBV.

Nasopharynx cancer or nasopharyngeal carcinoma (NPC) is the most common cancer originating in the nasopharynx, most commonly in the postero-lateral nasopharynx or pharyngeal recess or 'Fossa of Rosenmüller' accounting for 50% cases. NPC can arise in children and adults. NPC is significantly more common in certain regions of East Asia and Africa than elsewhere, and its pathogenesis is thought to have a viral, dietary, or genetic aspect. The disease is most common in males. NPC is a squamous cell carcinoma or an undifferentiated type.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, oral swab, cultured cells, e.g., primary cultures, explants, and transformed cells, stool, urine, esophagus biopsy tissue etc. A biological sample is typically obtained from a eukaryotic organism, which may be a mammal, may be a primate and may be a human subject.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); and Cassol et al., (1992); Rossolini et al., *Mol. Cell. Probes*, 8:91-98 (1994)). The terms nucleic acid and polynucleotide are used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the EBV genomic sequence or a portion thereof, which encodes a viral protein such as EBV nuclear antigen (EBNA) and latent membrane protein (LMP) or encodes a non-coding EBV RNAs such EBV-encoded small RNA (EBER) 1 or 2. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments may be designed to specifically amplify regions of EBV genomic sequence potentially harboring one or more of the risk alleles/SNPs shown in Table 1 or 2 of the disclosure. Also, the primers may be designed for specifically amplify only a segment of EBV genomic sequence containing the SNP or SNPs intended to be detected. In this disclosure the term "primer pair" means a pair of primers that hybridize to opposite strands a target DNA molecule or to regions of the target DNA which flank a nucleotide sequence to be amplified (e.g., containing a potential SNP relevant to the purpose of detection such as for assessing NPC risk). In this disclosure the term "primer site" means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target, e.g., a portion of EBV genomic sequence harboring a particular SNP such as one relevant to NPC risk, for example, one in Table 1 or 2) to be readily detectable.

The term "treat" or "treating," as used in this application, describes to an act that leads to the elimination, reduction, alleviation, reversal, or prevention or delay of onset or recurrence of any symptom of a relevant condition (e.g., NPC). In other words, "treating" a condition encompasses both therapeutic and prophylactic intervention against the condition: for example, upon testing positive to have any EBV variant harboring one or more of the NPC-risk SNPs set forth in Table 1 or 2, an individual who may not have any symptoms of NPC will follow a therapeutic or prophylactic regimen under the supervision of a medical professional such as eliminating salted foods from his diet. The individual may also follow a routine of regularly and frequently scheduled physical examinations to monitor for any early signs of NPC. For examples, plasma EBV DNA test or endoscopy examination may be performed. If the individual is diagnosed with NPC, standard radiotherapy and chemotherapy may be performed.

The term "effective amount" as used herein refers to an amount of a given substance that is sufficient in quantity to produce a desired effect. For example, when an effective amount of a therapeutic agent for treating NPC is administered to a patient, the symptoms of NPC are reduced, reversed, eliminated, prevented, or delayed of the onset in the patient. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, NPC. Subjects also include individuals currently undergoing therapy that seek manipulation of the therapeutic regimen. Subjects or individuals in need of treatment include those that demonstrate symptoms of NPC, or those at are at risk of suffering from NPC or its symptoms, or those have been tested positive for EBV variants harboring one or more of the NPC-relevant risk alleles or SNPs (e.g., one or more shown in Table 1 or 2) but may not may not have any family history and/or may or may not have any potentially relevant symptoms. For example, subjects in need of treatment include individuals with a genetic predisposition or family history for NPC, those that have suffered relevant symptoms in the past, those that have been exposed to a triggering substance or event, as well as those suffering from chronic or acute symptoms of the condition. A "subject in need of treatment" may be any gender and at any age of life.

The term "about" when used in reference to a predetermined value denotes a range encompassing ±10% of the value.

DETAILED DESCRIPTION

I. General

The present invention relates to EBV variants with newly identified genomic sequence variations, e.g., SNPs and indels, that are associated with risk of developing NPC or geographic location of the host individuals. This invention also provides methods of assessing NPC risk in individuals based on detection of one or more of NPC-associated SNPs or indels in EBV variants present in a biological sample obtained from the individuals.

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The polynucleotide sequence encoding a polypeptide of interest, e.g., an EBV protein or a fragment thereof, and synthetic oligonucleotides can be verified after cloning or subcloning using, e.g., the chain termination method for sequencing double-stranded templates of Wallace et al., *Gene* 16: 21-26 (1981).

II. Acquisition of Samples and Analysis of DNA

The present invention relates to detecting one or more SNPs or indels in the EBV genomic DNA found in a person's biological sample, especially a saliva sample or nasopharyngeal epithelial sample, as a means to detect the presence, to assess the risk of developing, and/or to monitor the progression or treatment efficacy of nasopharyngeal carcinoma (NPC). Thus, the first steps of practicing this invention are to obtain an appropriate sample from a test subject and extract DNA from the sample.

A. Acquisition and Preparation of Samples

An appropriate sample such as a saliva sample or a nasopharyngeal tissue sample is obtained from a person to be tested or monitored for NPC using a method of the present invention. Collection of a saliva or nasopharyngeal epithelial tissue sample from an individual is performed in accordance with the standard protocol hospitals or clinics generally follow. An appropriate amount of patient saliva or nasopharyngeal epithelium is collected and may be stored according to standard procedures prior to further preparation.

The analysis of EBV DNA found in a patient's sample according to the present invention may be performed using, e.g., saliva or nasopharyngeal lining tissue. The methods for preparing tissue samples for nucleic acid extraction are well known among those of skill in the art. For example, a subject's nasopharyngeal epithelial sample should be first treated to disrupt cellular membrane so as to release nucleic acids contained within the cells.

B. Detection of NPC-Risk Alleles in Genomic Sequence

The presence of one or more SNPs or indels relevant to NPC risk in a segment of EBV genomic sequence is investigated to provide indication as to whether a test subject is suffering from NPC, whether the subject is at risk of developing NPC at a later time, or whether the subject's NPC is worsening or improving. Typically, a segment of the EBV genomic sequence that includes an untranslated region or a region encoding a viral protein such as EBV nuclear antigen (EBNA) and latent membrane protein (LMP) or encoding a non-protein coding EBV RNAs such EBV-encoded small RNA (EBER) 1 or 2, is analyzed for the presence of one or more NPC-risk alleles or SNPs, such as those shown in Table 1 or 2.

1. DNA Extraction and Optional Amplification

Methods for extracting DNA from a biological sample are well known and routinely practiced in the art of molecular biology, see, e.g., Sambrook and Russell, supra. RNA and protein contamination should be eliminated to avoid interference with DNA analysis.

Following the isolation/purification of DNA from a biological sample taken from an individual being testing for risk/presence of NPC or for monitoring NPC progression, the DNA is then subjected to sequence-based analysis, such that the presence of specific risk allels/SNPs associated with NPC (e.g., one or more in Table 1 or 2) in EBV genomic sequence may be detected. An amplification reaction is optional prior to the sequence analysis.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

2. Sequence Analysis

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., from a non-risk allele to a risk allele) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

Alternatively, oligonucleotide primers specific for amplification of a segment of EBV genomic sequence harboring one or more SNPs or indels associated with NPC-risk may be used in an amplification reaction (such as a PCR) for the detection of such SNP(s). For example, the presence of such SNP(s) or indel(s) can be detected based on the presence of amplicon(s) resulted from amplification directed by the SNP-specific primer or primers. Optionally, such primer or primers can carry a detectable label for ease of detection. Further, oligonucleotide probes specific to a segment of EBV genomic sequence harboring one or more SNPs or indels associated with NPC-risk can be used to detect the presence of such SNP(s) in EBV genome based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., an amplified DNA containing one or more specific NPC-risk SNPs, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

EXAMPLES

The following examples are provided by way of illustration only and not by way of limitation. Those of skill in the art will readily recognize a variety of non-critical parameters that could be changed or modified to yield essentially the same or similar results.

Example 1: High Risk Epstein-Barr Virus Variants with Defined Genomic Characteristics are Strongly Associated with Nasopharyngeal Carcinoma This study reveals, for the first time, the presence of high risk EBV variants of NPC at the level of both loci and lineages. Further characterization of specific pathogenic mutations in the high risk EBV variants and survey of viral variants amongst different geographic populations will be important goals of future research. Analysis of EBV variants harboured in healthy individuals could be potentially developed as a novel screening method to assess the risk of NPC.

INTRODUCTION

Epstein-Barr virus (EBV) is a human gammaherpesvirus that infects the majority of the world's population and is strongly associated with Burkitt's lymphoma and epithelial malignancies such as nasopharyngeal carcinoma (NPC) and a subset of gastric carcinoma.[1] EBV is a double-stranded DNA virus whose genome is of approximately 170 kb in size and contains >86 open reading frames. The virus genome contains four major internal repeats (IR1 to IR4) and terminal repeats (TR). Nine latent proteins, including EBV nuclear antigen 1 (EBNA1), EBNA2, EBNA3A, –3B, –3C, EBNA-LP and latent membrane protein 1 (LMP1) and LMP2A, –2B are encoded by genes situated in the unique regions of the genome.[1] Other open reading frames encode capsid proteins, transcription factors as well as lytic proteins of various functions.[1] The virus also encodes non-coding EBV RNAs, such as EBV-encoded small RNA 1 (EBER1) and 2 (EBER2), BART-derived microRNAs (miRNAs-BARTs) and BHRF1 microRNAs (miRNAs-BHRF1).[2]

The incidence of NPC has a remarkable geographical distribution being 100-fold more frequent in Southeast Asia, North Africa and Alaska than the rest of the world[3], which prompted studies to investigate whether distinct variants of EBV might contribute to this disease. EBV genomes can be broadly classified into two distinct types, type 1 and type 2. The EBV types can be distinguished by the polymorphisms in EBNA2 and EBNA3A-C. Intertypic EBV containing type 1 EBNA2 and type 2 EBNA3A-C had also been reported.[4,5] EBV variants had been investigated in NPC tumours using various polymorphic genotype markers in the EBER1 and –2, LMP1, BHRF1, BZLF1 and EBNA1 loci in samples from different populations.[6-10] Particularly, the mutations in the transforming LMP1 gene were thought to be important in contributing to the pathogenesis of NPC.[11] However, studying genetic variations in a small number of candidate EBV genes is not sufficient to accurately assess the association between EBV genomic variations and NPC. A recent genomic study of EBV isolated from samples derived from different geographic areas and EBV-related diseases revealed worldwide EBV genetic diversity and suggested that NPC-derived EBV from endemic regions may be distinct from EBV variants derived from other regions.[5] Because genomic data are only available from a small number of NPC-derived EBV and those from healthy donor-derived EBV of the same population are largely absent, one cannot distinguish whether genetic differences between EBV derived from NPC and non-NPC samples are due to geographical variations or linked to pathogenesis. A genome-wide analysis of EBV variants isolated from NPC biopsies and those derived from the carriers of the same population is necessary to address this question.

This report is the first case-control study comparing genomic sequences of EBV isolated from saliva samples of 142 population carriers with those from primary tumour biopsies derived from 62 patients with NPC of Hong Kong. The data of this study reveal the presence of high risk EBV variants in most of the NPC patients (95%) and a subset of population carriers in Hong Kong (41%). These high-risk variants carry non-synonymous mutations in EBV lytic proteins and mutations which may affect the secondary structure of EBER2.

Materials and Methods

Participant Recruitment 894 subjects were recruited upon obtaining written consent to donate saliva samples for sequencing of EBV genomes harboured in population carriers of Hong Kong Chinese. All Hong Kong residents greater than 18 years old with no history of cancers or autoimmune diseases, but who may have medical conditions unrelated to EBV such as hypertension, are eligible to participate in the study. 62 NPC biopsies were obtained from the NPC Tissue bank of the Centre for Nasopharyngeal Carcinoma Research (CNPCR) and an established NPC tumour bank of inventors' laboratory. The collection of the NPC biopsies and saliva was approved by the Institutional Review Board (IRB) of The University of Hong Kong (HKU)/Hospital Authority Hong Kong West Cluster (IRB ref no. UW 08-156) for the purpose of EBV genome sequencing. High secretors of EBV, whose saliva samples contain $>/=1\times10^5$ copies of virus/ml, were selected for target capture of EBV genomes and sequencing. 180 saliva samples could meet the viral load criteria. The characteristics of the population carriers and NPC patients are shown in FIG. 5.

DNA Sample Preparation

DNA of tumour and saliva samples was extracted using AllPrep DNA/RNA Micro Kit and Qiagen Blood and Tissue Kit (Qiagen, Hilden, Germany) according to the manufacturer's protocol. NanoDrop spectrophotometer (Thermo Scientific) and Qubit dsDNA High Sensitivity (HS) Assay Kit (Life Technologies) were used to determine the concentration of the DNA samples.

Assessment of Viral Loads by Quantitative PCR

The viral loads of tumour and saliva samples were quantified by detecting the EBV BamH1W repeats in EBV genomes by quantitative PCR using ABI PRISM 7900 sequence detector (AppliedBiosystems, Life Technologies, CA).

Library Preparation, Target Capture and Sequencing 100 ng DNA of each sample was used for library preparation by NEBNext® Ultra™ DNA Library Prep Kit for Illumina® (New England Biolabs) followed by target capture of EBV genomes by Integrated DNA Technologies (IDT) xGen® Lockdown® probes and IDT Hybridization Kits. The IDT xGen® Lockdown® probes were 120 bp DNA oligos designed across the whole genome of type 1 EBV and selected regions of type 2 EBV. These oligos covered the genome at end-to-end (1x) coverage. The HiSeq 2500 Sequencer (100-bp paired-end) platform at the Centre for Genomic Sciences (CGS) of HKU was used to sequence the EBV genomes.

Genome Assembly

Assembly was generated that represents single dominant strain in every sample. Raw reads were trimmed using Trimmomatic (v0.36).[12] The first 2 bases and end bases with quality score below 28 were removed. Reads shorter than 70 bp were discarded. Reads were assembled into contigs using SPAdes (v3.11).[13] Kmer sizes of 69, 79 and 89 were used. Contigs longer than 500 bp and coverage >5 were output. The contigs were located using MiniMap2 (v2.11-r797).[14] The confounding effects of mixed infection were minimized by excluding samples with multiple contigs stacking outside repetitive sequences and OriLyt. Contigs were mapped, oriented and sorted using ABACAS (v1.3.2)[15] against NC_007605.1. Unmapped contigs were discarded and then NG50 was calculated using 171,823 as reference genome size. Highly fragmented assemblies (NG50<8000) were excluded to provide higher confidence that each assembly represents a single EBV genome. Ten nucleotides in each end of contigs were trimmed and gaps were narrowed with reads using GapFiller (v1.10).[16] The assemblies were aligned to NC_007605.1 using MUMmer (v3.23)[17] and linearized according to the configuration of NC_007605.1. Then, mixed infection effects were further controlled by assessing the heterogeneity in each base. Reads were mapped back to the draft genomes using BWA-MEM[18], PCR duplicates were removed using PICARD (website: broadinstitute.github.io/picard/), and reads were piled up with BCFtools (v1.7).[19] Bases were considered ambiguous if supported by fewer than 50% of high-quality bases in BCFTools [i.e. (AD of the allele on the assembly)/(total AD for all alleles +0.1)<0.5]. Ambiguous bases were substituted by 'N' and treated as missing data in subsequent analyses. Sequencing depths were estimated by the number of mapping reads mapped to genomic regions outside repetitive regions and OriLyt using the same alignment method. A summary of NG50, viral copies and sequencing depth is available in FIG. 6.

SNP Calling and Quality Control

Figure 13:
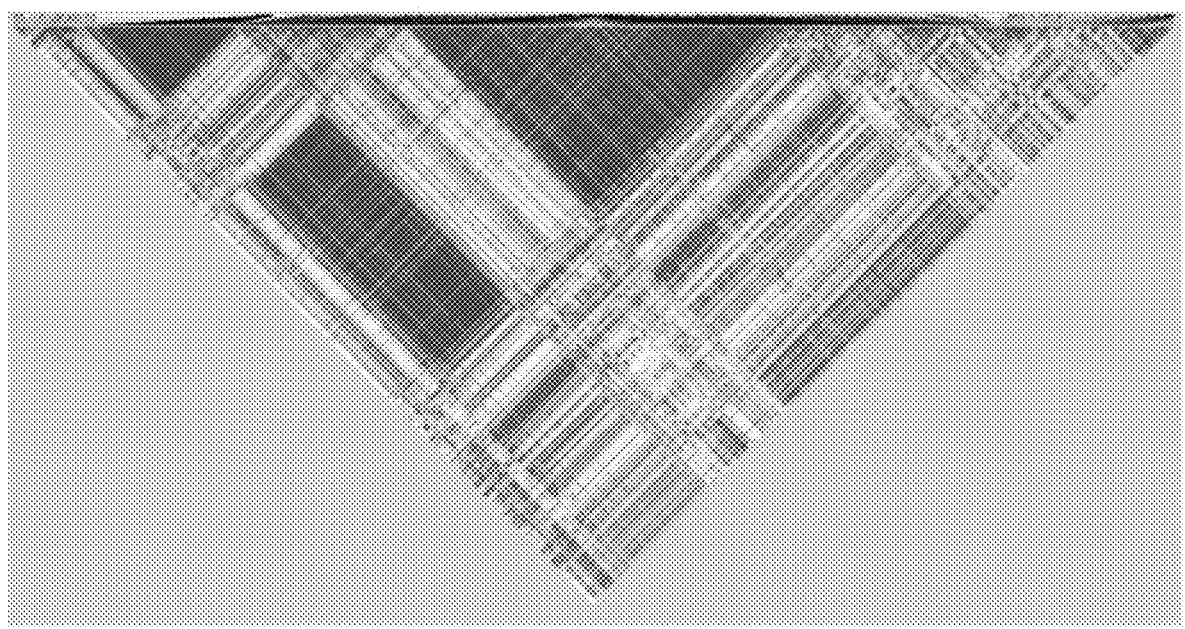
FIG. 13 Haploview diagram showing the linkage disequilibrium (LD) pattern of EBV genomes in Hong Kong. LD is observed along the EBV genome. The SNPs within EBNA2 and EBNA3A-C are most tightly linked. In addition, high LD is present between these two large blocks, supporting their genotypes pattern in different EBV types. Moreover, other linked SNPs are found to scatter across the genomes.

Assemblies were compared with NC_007605.1 using MiniMap2.[14] BCFtools[19] were used to call SNPs and mask repetitive regions and OriLyt to reduce inaccurate variant calls due to multiple copies of repeats and OriLyt. The EBV types were determined by the relative mismatch in EBNA2 and EBNA3 genes of the type 1 and type 2 reference genome (NC_007605.1 and NC_009334.1, respectively). Multiallelic SNPs were split into multiple biallelic SNPs using BCFtools norm. SNPs and sample were included with parameters: SNP with minor allele frequency (MAF) >0.05; SNP with missingness <0.1; and sample with missingness <0.2. The pattern of linkage disequilibrium was computed and visualized in Haploview[20] (FIG. 13). After all quality control steps, The Hong Kong dataset comprised of 142 controls and 62 NPC biopsies.

Analysis of Geographic Patterns Between Hong Kong EBV and Non-NPC Endemic EBV

Published EBV genomes from non-NPC endemic regions were selected from Genbank. EBV with unknown origins as well as those collected from Chinese/Vietnamese ethnicity or areas was excluded. Strains B95-8, Jijoye and SNU719 were resequenced and assembled using the same method in this study. In total, there are 97 assemblies of non-endemic origins were obtained. In addition to the 204 assemblies described above (142 controls+62 NPC biopsies), SNP calling and quality control procedures were carried out. Principal component analysis (PCA) was performed using PLINK v1.90.[21] The pairwise distance was computed using the genotypes in R. Hierarchical clustering and heatmap were computed with the default setting in R package pheatmap.[22] VCFtools[23] was used to estimate the weighted $F_{ST}$ values in 1000 nucleotide windows with 100 base-pair step size. The input genotypes were modified into homozygous diploid samples. In type 1 samples, EBV from non-endemic origins were compared with Hong Kong control to obtain genome-wide $F_{ST}$. Similarly, non-endemic EBV were compared with Hong Kong NPC. The regions with $F_{ST}$ uniquely high in NPC were shown by subtracting the $F_{ST}$ values for controls from NPC.

Cluster Analysis

To infer the subpopulations of the dataset, Bayesian Analysis of Population Structure (BAPS) 6.0 was used to cluster samples.[24] SNPs with MAF<0.05 (excluded in GWAS) were also included. The maximum number of populations were tested from 2 to 7. Admixture analysis was performed using default parameters. Results were visualized using R package pophelper.[25] The Hamming distance was used in the distance matrix to generate a neighbour joining tree using R package ape.[26] $F_{ST}$ statistics for each SNP and weighted $F_{ST}$ statistics in sliding 1000 nucleotide windows were calculated between populations using VCFtools[23] as described above. The association between subgroups and NPC was assessed with chi-square test in R. The overrepresentation of NPC EBV in each subgroup was tested with hypergeometric test implemented in R.

Phylogenetic Analysis

The sequence alignment was generated by concatenating SNPs (MAF<0.05 also included) with missing genotypes coded as 'N'. The alignment was trimmed by automated algorithm in trimAl v1.4.[27] Maximum-likelihood trees were constructed under a general time reversal model with ascertainment bias correction (GTR+ASC) in IQ-TREE.[28] Fast tree search mode was chosen. The tree was visualised and annotated using ggtree.[29]

Principal Component Analysis (PCA) and Association Test for PCs and SNPs.

PCA and tests for PCs were performed in R package bugwas.[30] The same set of SNPs in association tests were used. Missing data was imputed using BEAGLE (v5.0).[31] The output from phylogenetic analysis was used for the tree input file. Bonferroni correction of p-value cut-off of 2.45× $10^{-4}$ was used to assess the significance of the 204 principal components. SNPs were also assigned to their most correlated PCs by bugwas. To test the association between each SNP and NPC, each SNP was fit in a logistic regression model adjusting for sex and age using PLINK v1.90[21], without including PCs as covariates in order to maximize the power for detecting variants correlated to NPC-associated lineages.

Genome-Wide Association Study (GWAS) Using Linear Mixed Model.

To control for population structure, a GWAS was performed using a linear mixed model implemented in GEMMA[32] provided by bugwas.[30] A relatedness matrix among genomes was generated with SNPs. Then SNPs were tested under linear mixed model adjusting for age and sex as fixed effects and relatedness matrix as random effects. The p-values from likelihood ratio tests were reported. Bonferroni correction was applied to set the genome-wide significance cut-off at $1.75 \times 10^{-5}$. False discovery rate (FDR) was controlled at 0.05. Median method was used to calculate genomic inflation factor lambda with R package GenABEL.[33]

Haplotype Association

The haplotypes formed by 24 significant SNPs, identified in GWAS by Bonferroni correction for p-values and controlling for FDR at EBER locus, were identified in NPC and controls. The presence/absence of each haplotype was coded as 1 and 0 and retested under the linear mixed model, including age and sex as fixed effects and the same relatedness matrix generated form SNPs in GWAS as random effects. The p-values were also derived from likelihood ratio test.

RNA Secondary Structure Prediction

The secondary structure of EBER2 was analyzed using RNAstructure version 6.0.1[34] with default parameters. The structures with lowest free energy are reported.

Genetic Risk Score Calculation

For each sample, genetic risk score was calculated from a set of specified SNPs. It was calculated as the sum of beta weighted by the presence/absence (coded as 1 or 0) of risk alleles, divided by the number of non-missing genotypes the sample has. The beta resulting from GEMMA output in GWAS was used. Other Chinese NPC sources include cell lines C666-1, M81, NPC43 (resequenced in this study), biopsies GD2 and D3201, and NPC saliva GD1. Chinese lung cancers included LC1-LC4. Chinese gastric cancers included EBVaGC1 to −9 and GC-variant-1 to −3.

Data Availability

Raw sequencing reads can be accessed on NCBI Sequencing Read Archive with accession number SRP152584. Assemblies were deposited on GenBank MH590370-MH590579.

Results

Figure 6:
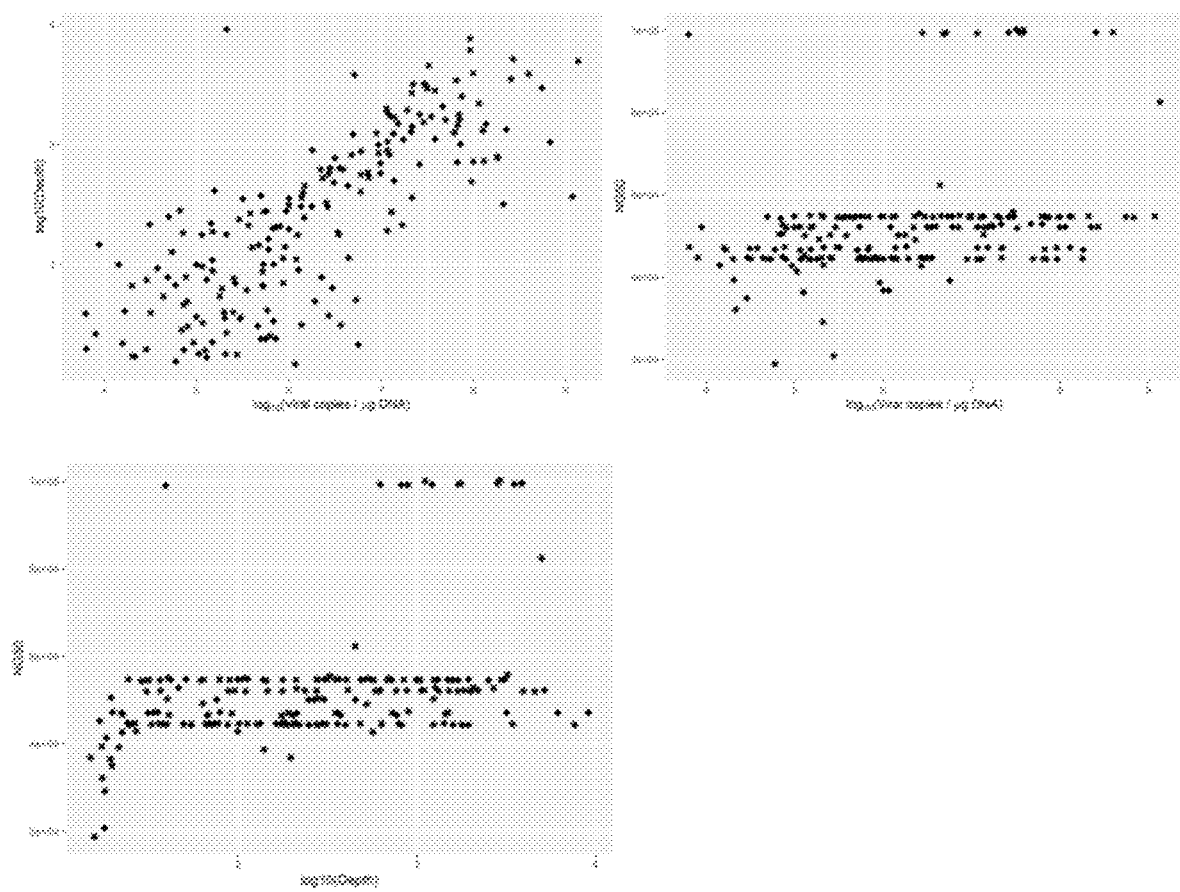
FIG. 6 Summary of the sequencing results. Pairwise patterns among sequencing depth, assembly quality measured by NG50 and viral copies are plotted.
Figure 7:
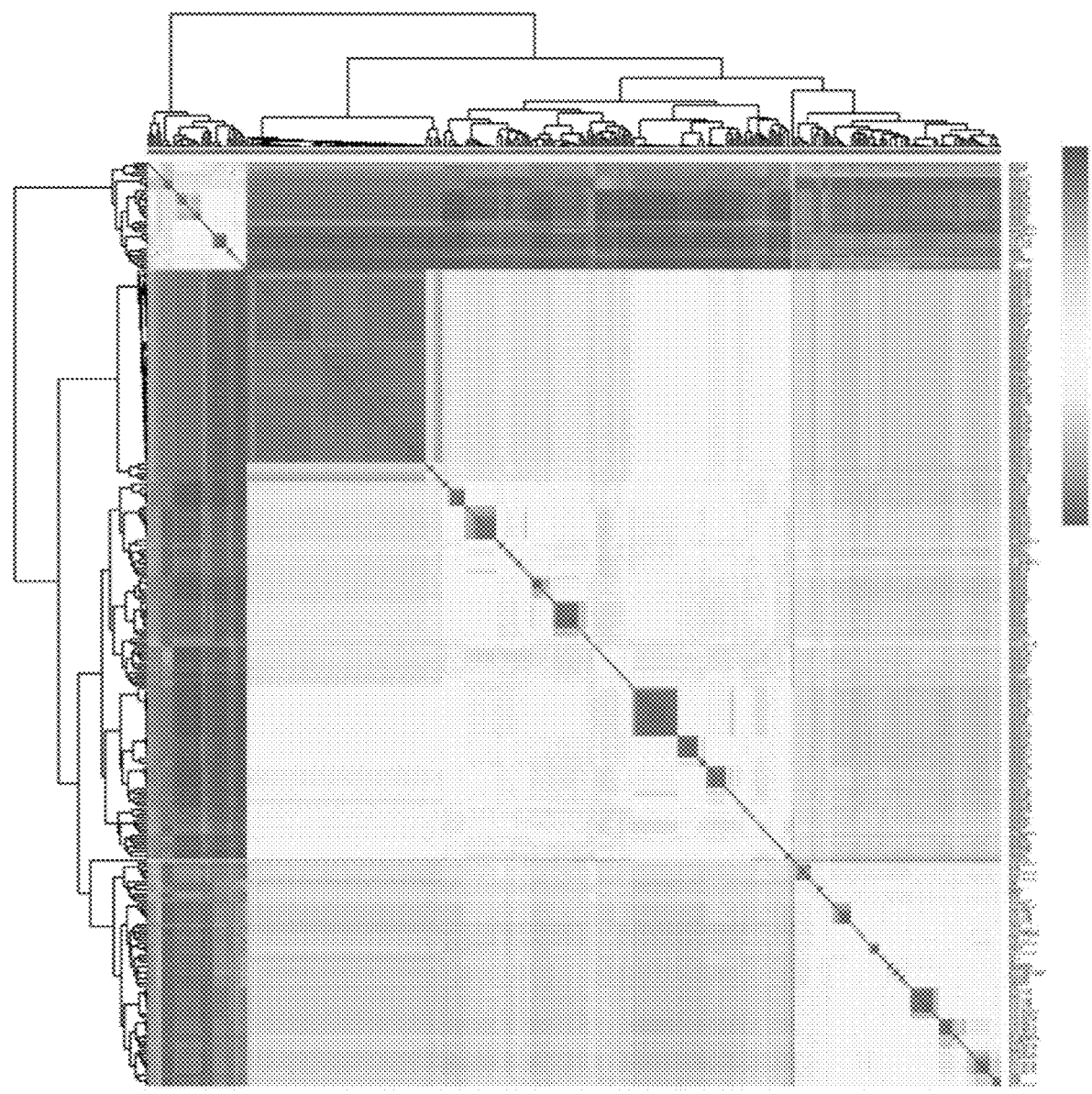
FIG. 7 Large size figure for hierarchical clustering of pairwise distance amongst EBV genomes. The sample names are indicated on the right, whereas the source information is displayed in the column.

The Genomes of EBV Isolated in Hong Kong Chinese are Genetically Distinct from Those Derived from Other Geographic Regions EBV genomes isolated in saliva of 142 population carriers and tumour biopsies of 62 NPC patients in Hong Kong were sequenced and assembled, in which HKNPC1-9[35] were resequenced (FIGS. 5 and 6). The data were compared with 97 published EBV genomes from non-NPC endemic regions. The total 301 genomes captured 11,040 single nucleotide polymorphisms (SNPs). Principal component analysis (PCA) was performed to visualize their genetic pattern (FIG. 1a). The first two PCs account for 39.2% and 17.1% respectively of the total variance. The first PC separates the type 1 and type 2 EBV, which are defined by the polymorphisms in EBNA2 and EBNA3A-C. Four intertypic EBV genomes are found in the data of this study, in which three of them carry type 1 EBNA2 and type 2 EBNA3A-C, consistent with the most commonly reported intertypic genotypes.[5] The remaining intertypic strain, found in an NPC biopsy, contains a rare combination of type 1 EBNA2 and EBNA3A in addition to type 2 EBNA3B-C.[36] The second PC displays geographic difference between EBV variants derived from Hong Kong and non-endemic regions which can be confirmed by clustering EBV genomes based on their genetic distance (FIG. 1b, FIG. 8).

Figure 8:
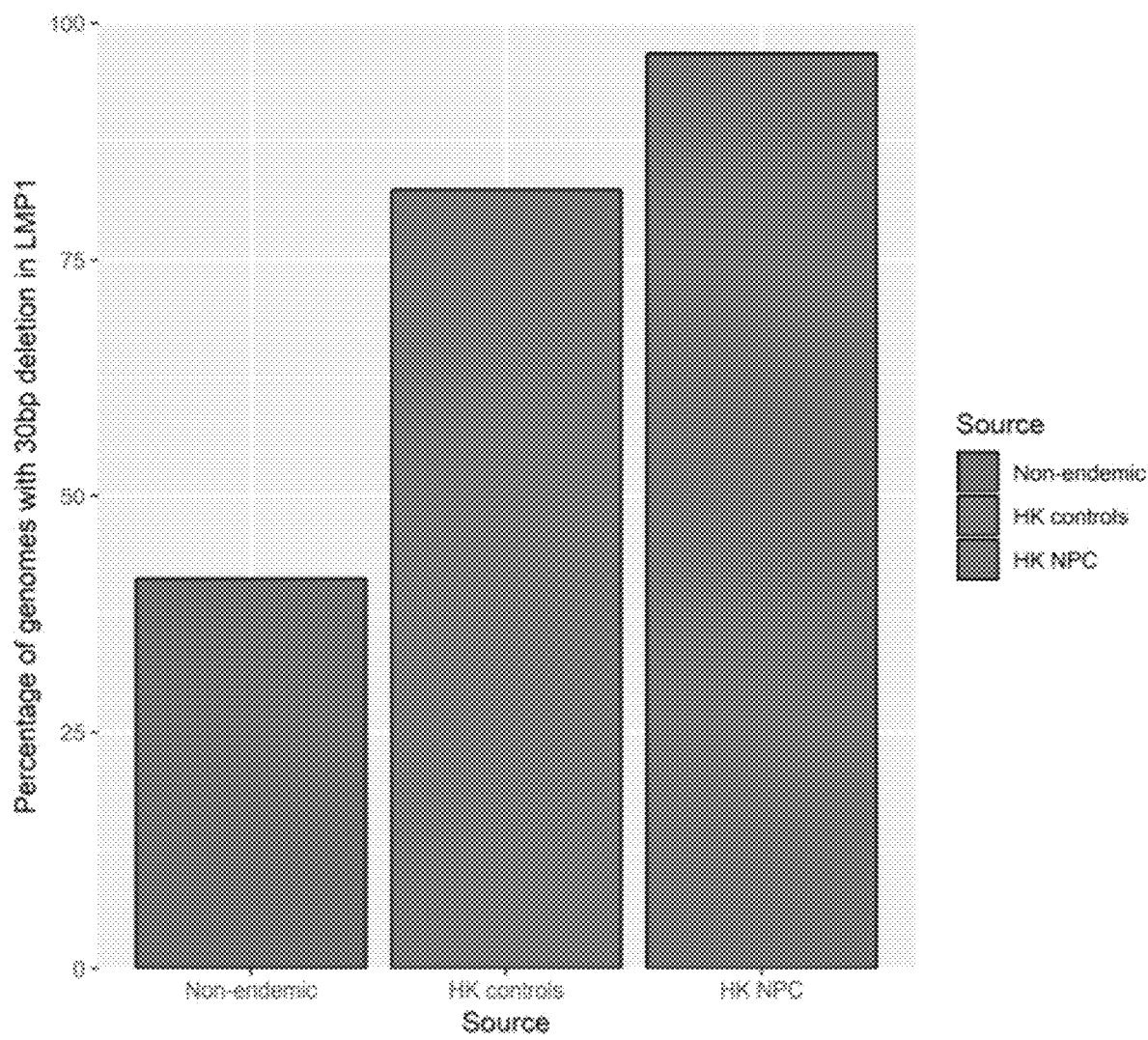
FIG. 8 The prevalence of 30 bp deletion in LMP1 in EBV genomes isolated from NPC patients and population carriers of Hong Kong and individuals from non-endemic regions.

LMP1 is one of the most important oncogenic proteins contributing to the pathogenesis of NPC.[37] Several variations in LMP1, particularly the 30-bp deletion between coordinates 167,808 to 167,837 (del-LMP1), were thought to be associated with NPC.[38] However, this del-LMP1 variant is highly prevalent in EBV derived from both population carriers and NPC tumours of Hong Kong, consistent with previous findings that the del-LMP1 represents a geographic variation rather than a disease-associated variation[39] (FIG. 8). In addition, a number of variations which differentiates the EBV variants in Hong Kong (both control and NPC) and non-endemic regions is identified (FIG. 1c). Analysis of EBV genomic variations without comparison with population control would risk identifying the geographic variations as disease-associated variations. Interestingly, genomic variations were observed which may be specific to NPC-derived EBV in comparison with control EBV in the regions near EBERs and other genes such as LF3, BALF4 and BALF5 (FIG. 1c).

Figure 9:
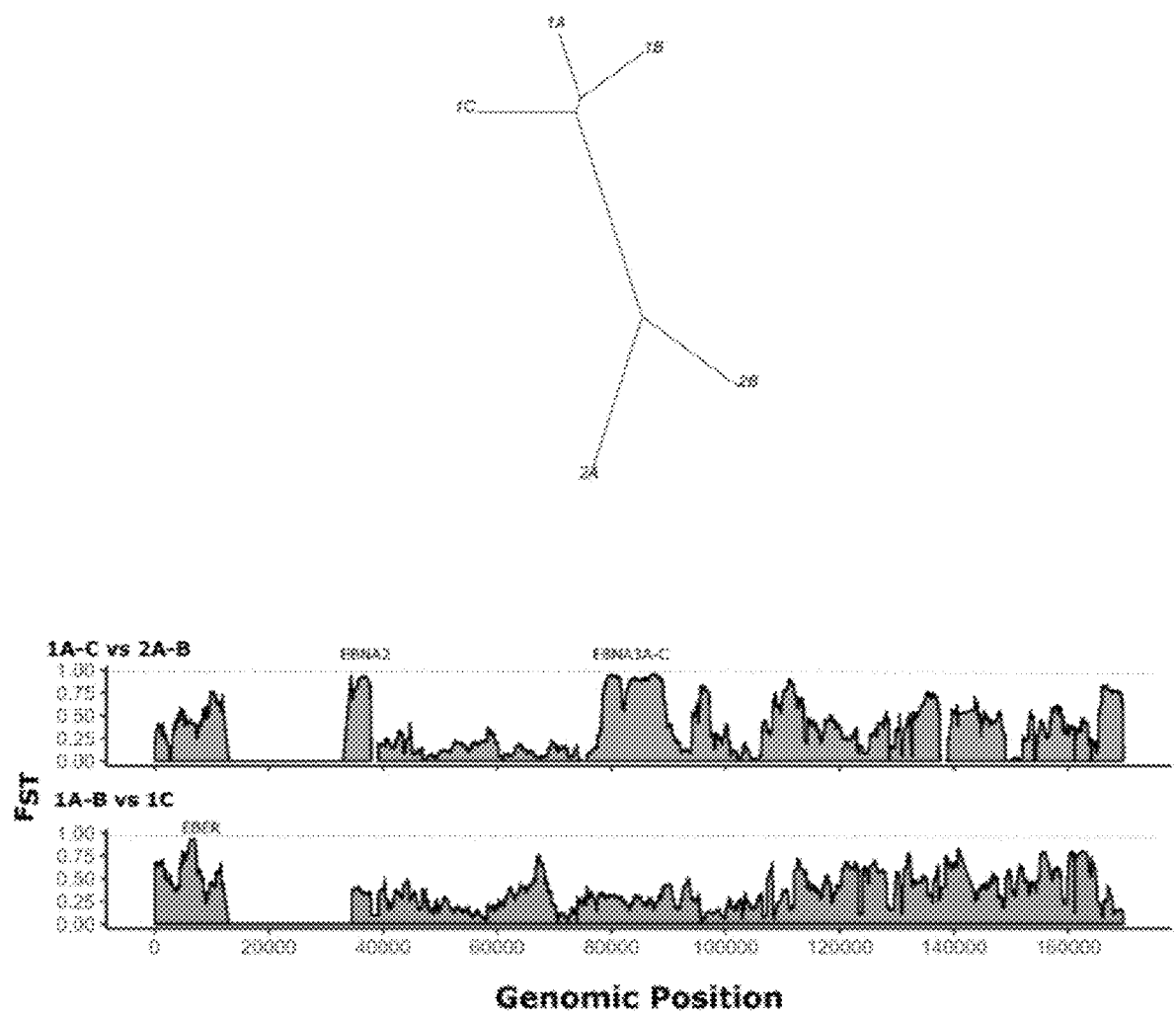
FIG. 9 (Upper) Neighbour-joining tree of the five subgroups identified using BAPS. Hamming distance matrix was used to construct the tree. (Lower) The genome-wide FST showing the differentiation between subpopulations in each 1000 nucleotide window. For example, in the comparison between subgroups 1A-C and subgroups 2A-B, regions near EBNA2 and EBNA3A-C are best separating them. Further, when comparing subgroups 1A-B with subgroup 1C, the most prominent difference mapped to the region near EBER.

Identification of Five EBV Subgroups 1A-C and 2A-B Amongst the Population Carriers in Contrast to the Predominance of 1A and -B in the Majority of NPC Two approaches, cluster analysis and PCA, were next employed to assess lineage-level association between EBV variants and NPC. First, all variants derived from NPC cases and controls were clustered using Bayesian Analysis of Population Structure (BAPS)[24] and five clusters with sizes of 45, 73, 66, 4 and 16 were identified, which are designated as subgroups 1A, 1B, 1C, 2A and 2B, respectively (FIG. 2a). Whilst the five subgroups account for 16.9%, 24.6%, 44.4%, 2.8% and 11.3% of control saliva-derived EBV, respectively, almost all NPC-derived EBV variants belong to subgroups 1A (33.9%) and 1B (61.3%) with the remaining in subgroup 1C (4.8%). The strong association between subgroups and NPC ($p=1.84 \times 10^{-10}$) and the overrepresentation of NPC in subgroups 1A and 1B ($p=2.50 \times 10^{-3}$ and $p=1.42 \times 10^{-07}$, respectively) suggests that two major lineages of EBV are harboured in NPC. The neighbour joining tree of the subgroups shows that subgroups 1A and —B are more closely related than 1C (FIG. 9). To identify the genomic regions that characterize subgroups 1A and —B, the EBV genome was scanned across with a 1000-nucleotide sliding window, and regions with high fixation index ($F_{ST}$) were identified, which reflects the population differentiation due to genetic structure (FIG. 9). The windows near the EBER region (coordinates 6328-7355) best separate subgroups 1A and —B from 1C ($F_{ST}=0.931$).

Figure 10:
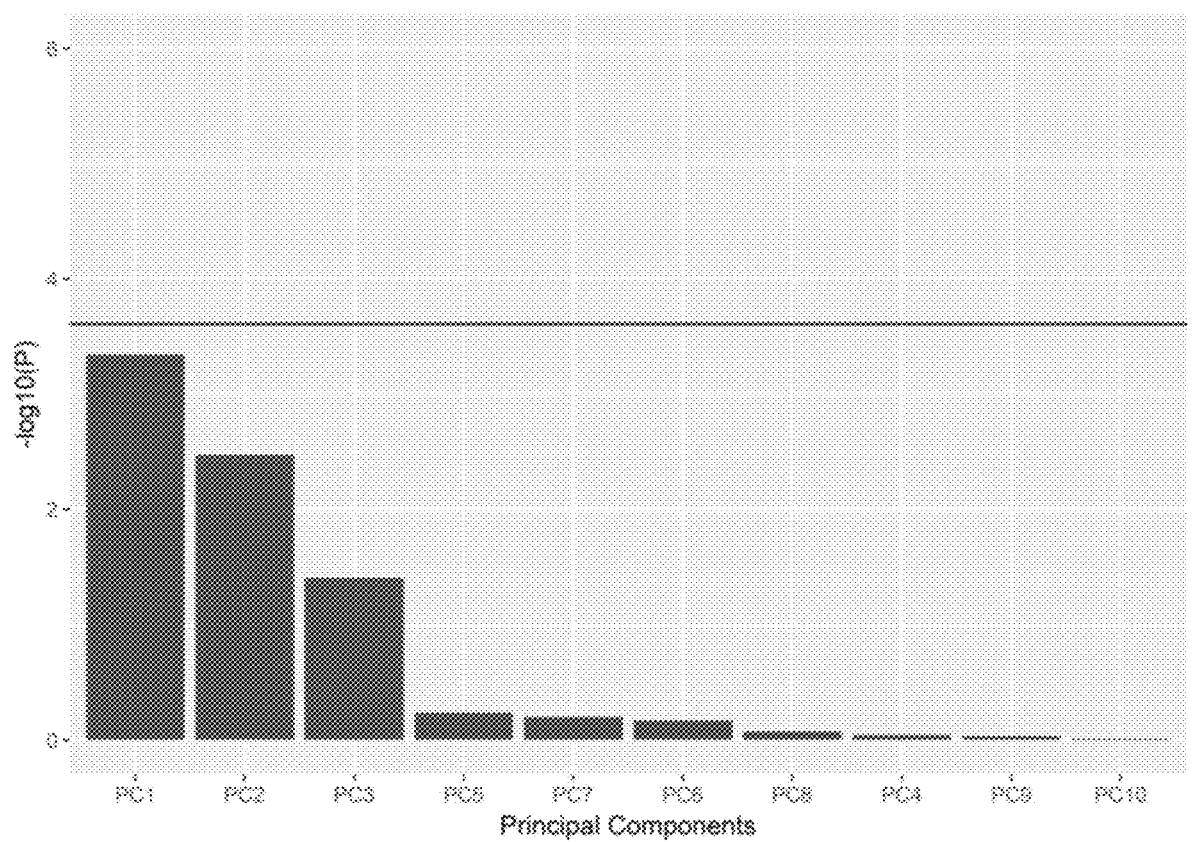
FIG. 10 Wald test of principal components (PCs) by bugwas. Only top 10 PCs are shown, ordered by the p-values. The horizontal line represents Bonferroni corrected P-value cut-off of $2.45\times10^{-4}$.

Second, the population structure was examined using PCA. consistent results between cluster analysis and PCA were observed, where subgroups are well stratified in the first two PCs (FIG. 2b). NPC-derived EBVs, which are characterized by subgroups 1A and —B, are found to cluster together in the phylogenetic tree corresponding to a region at a negative value of PC1 (FIG. 2c). The R package bugwas software was used to assess the association between the PCs and NPC as well as assigned every tested SNP to its most correlated PCs[30] (FIG. 10). At the cut-off p-value of 2.45×

$10^{-4}$, association between PC1 and NPC is just below the level of statistical significance ($p=5\times10^{-4}$). The association between SNPs and NPC was tested with a logistic regression model adjusting for age and sex (FIG. 2d). It was found that most significant SNPs were assigned to PC1, supporting the significance of PC1. These SNPs constitute 83 SNPs involving EBER and a number of genes, amongst which 12 will lead to non-synonymous changes in amino acids encoding DNA binding protein (BALF2), tegument protein (BNRF1, BTRF1), viral nuclease (BALF3), capsid antigen (BCLF1), scaffold protein (BVRF2 and BDRF1) and glycoprotein (BALF4 and BDLF3) (Table 2).

Figure 11:
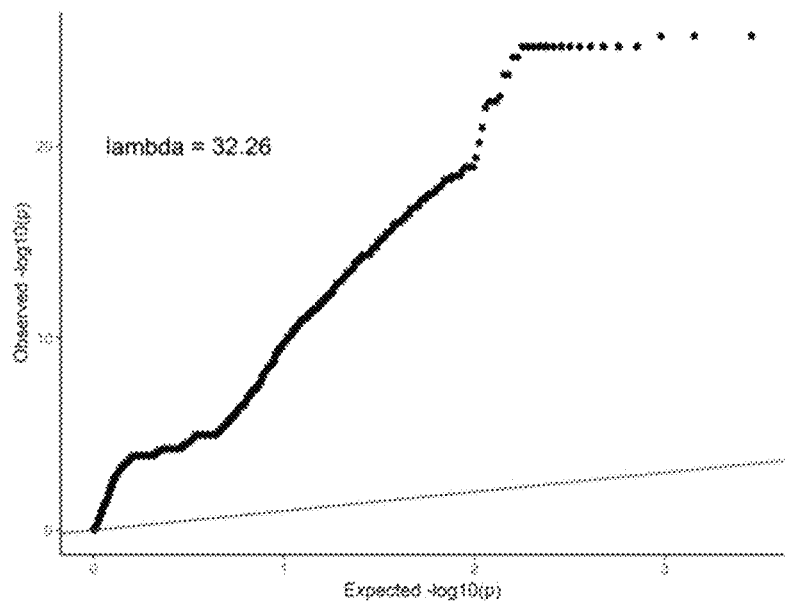
FIG. 11 Quantile-Quantile plot for genome-wide association study using (upper) chi-square test and (lower) linear mixed models. The classical study in discovering association between EBV variation and NPC relied on direct comparison of the allele counts with Chi-square tests. It was observed that application of this methods on the data of this study shows systemic inflation from the null distribution of p-values. The linear mixed model which consider genetic similarities among samples show better control of the inflation, where most SNPs close to the expected null and deviation seems to be limited to a small number of significant SNPs.
Figure 11:
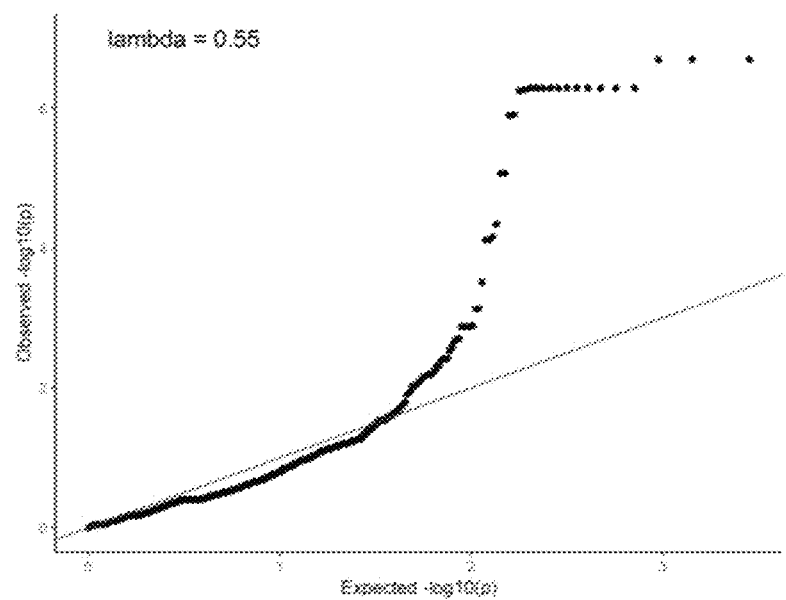

Genome-Wide Association Study Identifies the Strongest NPC-Associated SNPs in the EBER Region Population structure can be a potential confounding factor in the analysis of NPC-associated variations.[40] In order to identify the most robust SNPs that are associated with NPC, a genome-wide association study (GWAS) was carried out using GEMMA.[32] The significance of 2850 common SNPs (minor allele frequency >5%) was tested under a linear mixed model (LMM) that includes age and sex as fixed co-variates and genetic similarities among samples as a random effect and reduces the genomic inflation factor, lambda, to 0.55 (FIG. 11). The chip heritability, which reflects the proportion of variance in the phenotype explained by the tested SNPs, was 18.00% with a standard error of 7.42%, supporting the contribution of EBV genetics. At the Bonferroni corrected cut-off p value of $1.75\times10^{-5}$, the most significant SNPs associated with NPC were found in the EBER region (FIG. 3a; Table 1). The 20 most significant SNPs map to a region overlapping with EBER1, EBER2 and OriP (coordinates 6484-7327). The top three SNPs are located between EBER1 and EBER2 at coordinates 6866, 6884 and 6886 ($p=2.01\times10^{-7}$). Since Bonferroni correction could be too stringent for EBV genomes which contain highly linked SNPs, p-values were adjusted by controlling false discovery rate (FDR) at 0.05. This identified 3 additional SNPs near the EBER region (coordinates 5850, 6584 and 8568), 1 SNP (coordinate 5399) causing p.Val1222Ile in BNRF1 and 1 SNP (coordinate 137316) causing p.His560Pro in BVRF2.

Figure 12:
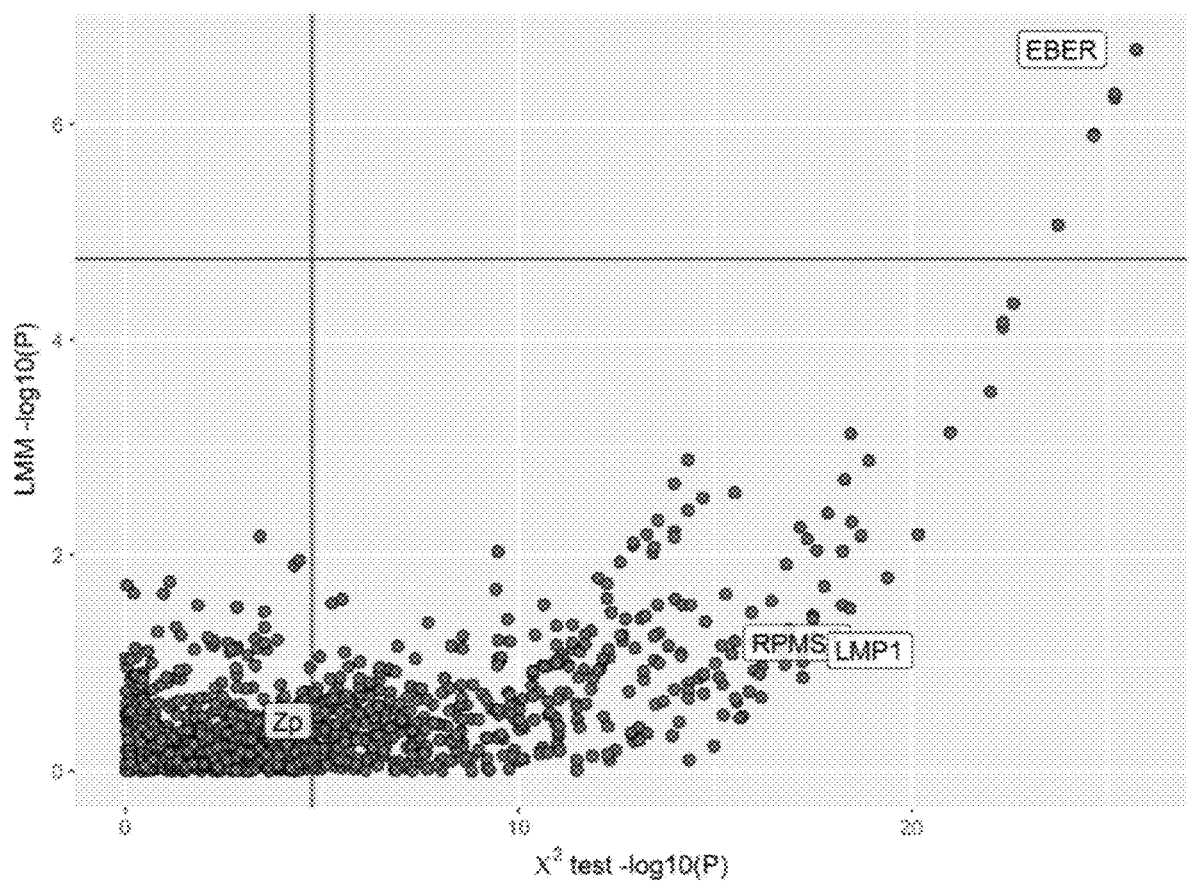
FIG. 12 Comparison between the p-values obtained from (x-axis) chi-square test and (y-axis) linear mixed models. Red lines represent genome-wide significant cut-off at $P=1.75\times10^{-5}$. A number of SNPs will pass the cut-off using the traditional approach, increasing the chance of detecting spurious association. In linear-mixed model, where the population structure is corrected, most significant SNPs in chi-square tests, including a proposed SNPs in RPMS1 and LMP1, failed to reach the cut-off. Only SNPs in EBER region remain.

Whilst polymorphisms in EBER41, RPMS1[42], Zp[43] and LMP1[11] had been proposed to be associated with NPC, these studies were based on data derived from pre-selected candidate genes and are prone to detect spurious association due to failure to adjust for the effects of population stratification.[40] To illustrate this point, significant association was found between reported genetic polymorphisms, such as G155391A in RPMS1 ($p=1.84\times10^{-17}$) and C167859T in LMP1 ($p=1.39\times10^{-18}$), and NPC by chi-square test in our case-control dataset (refer to FIG. 12). However, none of them reached genome-wide significant level of $1.75\times10^{-5}$ in the LMM where population stratification is corrected. In contrast, the SNPs in the EBER region remain highly significant.

NPC-Associated Haplotype in EBER Region Causes Structural Changes in EBER2

A total of 24 SNPs in the EBER region constitutes 12 haplotypes, with one dominant haplotype in NPC and two dominant haplotypes in control saliva (refer to FIG. 3b). Only 4 SNPs located in the intergenic region between EBER1 and -2 are conserved in former (refer to FIG. 3b). The distributions of these major haplotypes were significantly different between NPC and controls. The dominant NPC haplotype was found in 93.5% (58/62) of NPC-derived EBV variants and 39.4% (56/142) of control saliva-derived EBV. Meanwhile, the two dominant control haplotypes, which are different from the NPC haplotype, accounted for only 1.6% (1/62) of NPC-derived EBV and 57% (81/142) of control saliva-derived EBV. Under the LMM, the association between the dominant NPC haplotype and disease is found to reach statistical significance ($p=1.20\times10^{-5}$).

Amongst the 24 SNPs in the EBER region, it is hypothesized that the SNPs in EBER2 may have functional significance. EBER2 is a non-protein coding RNA thought to have direct interaction with both viral and cellular proteins or nucleic acids through its multiple stem loops.[44] The EBER2 variants dominant in NPC contain variations in RNA coordinates 44, 46, 57, 61, 93 and 170. Structural changes were observed in the first stem loop of EBER2 upon prediction by RNAStructure[34] (FIG. 3c). The first stem loop of EBER2 of wild type EBV consists of an internal loop, a bulge loop and a hairpin loop whereas the internal loop changes to two bulge loops and the original bulge loop and hairpin loop are altered in both structure and sequence in that of EBER2 of NPC-derived EBV. The first stem loop of EBER2 may be involved in the recruitment of cellular transcription factor such as PAX5 to the terminal repeat region of EBV thus can potentially modulate the transcription of LMP1.[44]

Classification of Risk Variants of EBV for NPC

Finally, a genetic risk score (GRS) was constructed based on the statistical effect sizes derived from GWAS to compare EBV variants isolated from different types of samples and geographic regions. Using the 25 SNPs outlined in Table 1, it was found that the GRS of EBV from non-endemic regions is generally lower than that of NPC-derived EBV, with the exception of the variant known as VGO from Brazil (FIG. 4a). On the other hand, 5 out of 6 EBV genomes isolated from cell lines (M81, C6661 and NPC43), biopsies (GD2, D3201) and saliva (GD1, lowest GRS) derived from NPC patients have very high GRS. In contrast, EBVs derived from all reported Chinese EBV-positive gastric cancers have zero GRS and only one of 4 EBV-positive lung cancers has high GRS. A similar trend is observed when we include the SNPs assigned to PC1 (refer to Table 2) that are found to be significant (FIG. 4b). The difference in GRS between EBV derived from NPC and non-NPC samples indicates the possibility of using EBV genomic variations in classifying risk variants of EBV for NPC.

Discussions

Previous case-control studies based on analysis of candidate EBV genes have reported association between various genetic polymorphisms and NPC.[11, 41-43] However, these studies are prone to detect spurious association due to the failure to adjust for the confounding effects of population stratification.[40] To minimize the confounding effects, it is essential to analyze individual SNP of EBV genome in the context of genome-wide sequence data in order to accurately identify significant variations associated with NPC. Whilst a number of SNPs, including G155391A in RPMS1 and C167859T in LMP1, are found to be associated with NPC by chi-square test in our case-control dataset (refer to FIG. 12), neither reach genome-wide significant level of $1.75\times10^{-5}$ in the linear mixed model (LMM) where population stratification is corrected.

The results of this GWAS suggest that the variations in the EBER region are the most robust ones in the context of the genetic background of EBV variants harboured in Hong Kong Chinese. Apparent association between some of these variations in the EBER region and NPC by a candidate gene approach in individuals of South China has been reported.[41] Functionally, several studies have indicated the link between EBERs and NPC by their abilities to promote cell growth and survival[45-48] and modulate the expression of LMP1 and LMP2 genes.[44] Based on previous functional experiments and the predicted alteration in the secondary structure of EBER2 (refer to FIG. 3c), it is postulated that EBER2 may play an important role in the development of NPC. In addition to the SNPs in the EBER region, a panel of SNPs that may be associated with the development of NPC is also identified (refer to FIG. 2d and Table 2). Twelve of these SNPs will lead to non-synonymous changes in amino acids of EBV lytic proteins, which include DNA binding protein, tegument protein, viral nuclease, capsid antigen, scaffold protein and glycoprotein.

The results of this study may not be able to reveal all possible NPC risk loci on the EBV genome. First, one may lose statistical power for detecting other risk loci when correcting for population structure, in exchange for lower false discovery rate.[49] However, these missed genetic variants are likely to be assigned to PC1 as shown in FIG. 2d and Table 2. Meta-analysis of studies with larger sample size as well as similar studies in other NPC-endemic regions will increase the chance to discover these variations. Second, the variations in the repetitive regions are not examined due to the limitation of short-read sequencing. Further studies utilizing long-range sequencing platforms will help to interrogate the association between variations in repetitive regions and NPC. Third, interaction between host genetics[50-53], environmental exposures and viral variants has not been explored. A joint study of EBV and host genomics may provide new insights into such interactions. Last, sequencing of EBV genomes is feasible in about 20% of the saliva samples due to the requirement of high viral copy number for efficient capture of EBV DNA. Further optimization of the target capture protocol will enable sequencing of EBV in a higher percentage of samples.

In conclusion, the present inventors have identified high risk EBV variants of NPC at the level of both loci and lineages through a genome-wide case-control study. The presence of high risk EBV variants in the majority of NPC biopsies and a proportion of population carriers of Hong Kong support an important role of EBV genetic variations in the pathogenesis of NPC and explain the high incidence of NPC in endemic area such as Hong Kong. Further characterization of specific pathogenic mutations in the high risk EBV variants and survey of viral variants amongst different geographic populations will be important goals of future research.

All patents, patent applications, and other publications, including GenBank Accession Numbers or equivalent sequence identification numbers, cited in this application are incorporated by reference in the entirety of their contents for all purposes.

TABLE 1

The most significant NPC-associated SNPs and indels identified in the GWAS.

| Coordinates | Risk allele | Non-risk allele | Freq NPC | Freq Control | FDR adjusted P | P-value | Annotation |
|---|---|---|---|---|---|---|---|
| 5399 | A | G | 0.93548 | 0.4085 | 0.0112059 | $9.98 \times 10^{-05}$ | p.Val1222Ile in BNRF1 |
| 5850 | T | A | 0.93548 | 0.4085 | 0.0112059 | $9.98 \times 10^{-05}$ | BNRF1 3' UTR |
| 6484 | T | C | 0.95161 | 0.4085 | 0.0014671 | $1.10 \times 10^{-05}$ | Between BNRF1 and EBER1 |
| 6584 | G | A | 0.93548 | 0.4085 | 0.0109174 | $8.98 \times 10^{-05}$ | Between BNRF1 and EBER1 |
| 6866 | A | G | 0.96774 | 0.4014 | 0.0001186 | $2.60 \times 10^{-07}$ | Between EBER1 and EBER2 |
| 6884 | G | A | 0.96774 | 0.4014 | 0.0001186 | $2.60 \times 10^{-07}$ | Between EBER1 and EBER2 |
| 6886 | T | G | 0.96774 | 0.4014 | 0.0001186 | $2.60 \times 10^{-07}$ | Between EBER1 and EBER2 |
| 6911 | A | G | 0.96774 | 0.4085 | 0.0001186 | $7.03 \times 10^{-07}$ | Between EBER1 and EBER2 |
| 6944 | G | A | 0.96774 | 0.4085 | 0.0001186 | $7.31 \times 10^{-07}$ | Between EBER1 and EBER2 |
| 6999 | G | T | 0.96774 | 0.4085 | 0.0001186 | $6.64 \times 10^{-07}$ | EBER2 |
| 7001 | T | A | 0.96774 | 0.4085 | 0.0001186 | $6.64 \times 10^{-07}$ | EBER2 |
| 7012 | G | A | 0.96774 | 0.4155 | 0.0002403 | $1.60 \times 10^{-06}$ | EBER2 |
| 7016 | T | A | 0.96774 | 0.4085 | 0.0001186 | $6.64 \times 10^{-07}$ | EBER2 |
| 7048 | C | A | 0.96774 | 0.4085 | 0.0001186 | $6.64 \times 10^{-07}$ | EBER2 |
| 7121 | C | CTA | 0.96774 | 0.4085 | 0.0001186 | $6.64 \times 10^{-07}$ | EBER2 |
| 7125 | G | T | 0.96774 | 0.4085 | 0.0001186 | $6.64 \times 10^{-07}$ | EBER2 |
| 7134 | C | G | 0.96774 | 0.4085 | 0.0001186 | $6.64 \times 10^{-07}$ | Between EBER2 and OriP |
| 7187* | A | AAACT | 0.96774 | 0.4014 | 0.0001186 | $1.91 \times 10^{-07}$ | Between EBER2 and OriP |
| 7198 | T | C | 0.96774 | 0.4085 | 0.0001186 | $6.64 \times 10^{-07}$ | Between EBER2 and OriP |
| 7206 | A | T | 0.96774 | 0.4085 | 0.0001186 | $6.64 \times 10^{-07}$ | Between EBER2 and OriP |
| 7213 | C | G | 0.96774 | 0.4085 | 0.0001186 | $6.64 \times 10^{-07}$ | Between EBER2 and OriP |
| 7233 | A | G | 0.95161 | 0.4085 | 0.0014671 | $1.11 \times 10^{-05}$ | Between EBER2 and OriP |
| 7262 | A | G | 0.96774 | 0.4085 | 0.0001186 | $6.64 \times 10^{-07}$ | Between EBER2 and OriP |
| 7297 | T | C | 0.96774 | 0.4155 | 0.0002403 | $1.65 \times 10^{-06}$ | Between EBER2 and OriP |
| 7327 | C | T | 0.96774 | 0.4085 | 0.0001186 | $6.64 \times 10^{-07}$ | OriP |
| 8568 | T | A | 0.93548 | 0.4043 | 0.0075797 | $5.97 \times 10^{-05}$ | OriP |
| 59515 | CCTCCTT | C | 0.95161 | 0.4789 | 0.0290621 | $2.79 \times 10^{-04}$ | p.Gly1145_Gly1146insGluGly in BOLF1 |
| 59518 | CCTCCTA | C | 0.95161 | 0.4789 | 0.0168752 | $1.56 \times 10^{-04}$ | p.Gly1144_Gly1145insValGly BOLF1 |
| 137316 | C | A | 0.91935 | 0.3944 | 0.0396853 | $3.94 \times 10^{-04}$ | p.His560Pro in BVRF2 |

NC_007605.1 is used as a reference EBV genome for variants calling. The table shows the SNPs and indels that pass false discovery rate (FDR) adjusted P of 0.05 in FIG. 3a. Genome-wide significant cut-off of $P = 1.75 \times 10^{-5}$ was used.
*The most significant indel.

TABLE 2

SNPs assigned to PC1 pass genome-wide significance cut-off under logistic regression model

| Coordinate | Risk allele | Odd ratio | P in logistic regression | Frequency in non-endemic origins | Frequency in NPC | Frequency in Control | Gene | Nonsynonymous (N)/ synonymous (S) | Annotation |
|---|---|---|---|---|---|---|---|---|---|
| 6866 | A | 6.85 | 2.28E−07 | 0.0206186 | 0.96774 | 0.4014 | | | |
| 6884 | G | 6.85 | 2.28E−07 | 0.360825 | 0.96774 | 0.4014 | | | |
| 6886 | T | 6.85 | 2.28E−07 | 0.360825 | 0.96774 | 0.4014 | | | |
| 6999 | G | 6.74 | 2.87E−07 | 0.0103093 | 0.96774 | 0.4085 | | | |
| 7001 | T | 6.74 | 2.87E−07 | 0.0103093 | 0.96774 | 0.4085 | | | |
| 7016 | T | 6.74 | 2.87E−07 | 0.0103093 | 0.96774 | 0.4085 | | | |
| 7048 | C | 6.74 | 2.87E−07 | 0.0103093 | 0.96774 | 0.4085 | | | |
| 7125 | G | 6.74 | 2.87E−07 | 0.0103093 | 0.96774 | 0.4085 | | | |
| 7134 | C | 6.74 | 2.87E−07 | 0.0206186 | 0.96774 | 0.4085 | | | |
| 7198 | T | 6.74 | 2.87E−07 | 0.0103093 | 0.96774 | 0.4085 | | | |
| 7206 | A | 6.74 | 2.87E−07 | 0.0103093 | 0.96774 | 0.4085 | | | |
| 7213 | C | 6.74 | 2.87E−07 | 0.0103093 | 0.96774 | 0.4085 | | | |
| 7262 | A | 6.74 | 2.87E−07 | 0.0103093 | 0.96774 | 0.4085 | | | |
| 7327 | C | 6.74 | 2.87E−07 | 0.0103093 | 0.96774 | 0.4085 | | | |
| 6911 | A | 6.73 | 2.93E−07 | 0.360825 | 0.96774 | 0.4085 | | | |
| 6944 | G | 6.73 | 2.94E−07 | 0.412371 | 0.96774 | 0.4085 | | | |
| 7012 | G | 6.64 | 3.56E−07 | 0.0103093 | 0.96774 | 0.4155 | | | |
| 7297 | T | 6.63 | 3.59E−07 | 0.0103093 | 0.96774 | 0.4155 | | | |
| 156637 | A | 5.67 | 3.10E−06 | 0.0103093 | 0.96774 | 0.507 | BALF4 | N | p.Ala743Val |
| 6484 | T | 5.39 | 5.88E−08 | 0 | 0.95161 | 0.4085 | | | |
| 7233 | A | 5.39 | 5.89E−08 | 0 | 0.95161 | 0.4085 | | | |
| 160804 | C | 4.76 | 5.42E−07 | 0.597938 | 0.95161 | 0.507 | BALF3 | S | p.Val139Val |
| 140745 | G | 4.71 | 5.70E−07 | 0 | 0.95082 | 0.4539 | LF3 | | |
| 8568 | T | 4.67 | 2.21E−08 | 0.0108696 | 0.93548 | 0.4043 | | | |
| 6584 | G | 4.63 | 2.52E−08 | 0.319588 | 0.93548 | 0.4085 | | | |
| 5850 | T | 4.62 | 2.63E−08 | 0 | 0.93548 | 0.4085 | | | |
| 5399 | A | 4.62 | 2.63E−08 | 0 | 0.93548 | 0.4085 | BNRF1 | N | p.Val1222Ile |
| 135355 | T | 4.43 | 1.53E−06 | 0 | 0.95161 | 0.493 | BVLF1 | S | p.Ala91Ala |
| 134350 | G | 4.31 | 2.45E−06 | 0.0515464 | 0.95161 | 0.5141 | BVRF1 | S | p.Ala408Ala |
| 160827 | T | 4.25 | 1.63E−07 | 0.0103093 | 0.93548 | 0.4789 | BALF3 | S | p.Arg132Arg |
| 137316 | C | 4.14 | 1.55E−07 | 0 | 0.91935 | 0.3944 | BVRF2 | N | p.His560Pro |
| 155989 | A | 4.10 | 2.20E−08 | 0 | 0.91935 | 0.4085 | BALF5 | S | p.Leu100Leu |
| 140306 | C | 4.10 | 2.66E−07 | 0 | 0.93548 | 0.4507 | | | |
| 1535 | T | 3.99 | 8.47E−06 | 0 | 0.95161 | 0.5612 | | | |
| 153012 | G | 3.99 | 8.16E−06 | 0.175258 | 0.95161 | 0.5563 | | | |
| 140255 | A | 3.96 | 5.31E−07 | 0.0104167 | 0.93548 | 0.4789 | | | |
| 155391 | A | 3.92 | 7.20E−07 | 0 | 0.93548 | 0.493 | RPMS1, BALF5 | N | p.Asp51Asn, p.Leu300Leu |
| 1075 | T | 3.81 | 1.24E−06 | 0 | 0.93548 | 0.5 | LMP2 | S | p.Ile350Ile |
| 1195 | T | 3.80 | 1.31E−06 | 0 | 0.93548 | 0.5036 | LMP2 | S | p.Pro390Pro |
| 11695 | G | 3.70 | 2.63E−08 | 0 | 0.90323 | 0.4225 | | | |
| 160971 | C | 3.66 | 3.29E−08 | 0.0309278 | 0.90323 | 0.4296 | BALF3, BALF2 | N | p.Thr84Ala, p.Arg1114Arg |
| 132225 | C | 3.57 | 3.84E−07 | 0 | 0.91935 | 0.4718 | BXLF1 | S | p.Pro116Pro |
| 161036 | C | 3.57 | 5.65E−08 | 0.123711 | 0.90323 | 0.4296 | BALF3, BALF2 | N | p.Gln62Arg, p.Ser1093Gly |
| 132048 | A | 3.56 | 3.97E−07 | 0 | 0.91935 | 0.4648 | BXLF1 | S | p.Ala175Ala |
| 147686 | T | 3.55 | 6.69E−08 | 0.0104167 | 0.90323 | 0.4366 | | | |
| 158430 | T | 3.48 | 7.74E−07 | 0 | 0.91935 | 0.493 | BALF4 | S | p.Val145Val |
| 147311 | A | 3.46 | 1.21E−07 | 0.0104167 | 0.90323 | 0.4507 | | | |
| 147608 | T | 3.41 | 1.61E−07 | 0.0104167 | 0.90323 | 0.4577 | | | |
| 147652 | A | 3.41 | 1.61E−07 | 0.0104167 | 0.90323 | 0.4577 | | | |
| 163364 | T | 3.41 | 3.10E−08 | 0 | 0.8871 | 0.4085 | BALF2 | N | p.Val317Met |
| 147069 | T | 3.41 | 1.62E−07 | 0.0104167 | 0.90323 | 0.4507 | | | |
| 147683 | C | 3.40 | 1.79E−07 | 0.0104167 | 0.90323 | 0.4648 | | | |
| 147699 | A | 3.40 | 1.79E−07 | 0.0104167 | 0.90323 | 0.4648 | | | |
| 147709 | A | 3.40 | 1.79E−07 | 0.0104167 | 0.90323 | 0.4648 | | | |
| 1177 | T | 3.39 | 1.31E−06 | 0 | 0.91935 | 0.4964 | LMP2 | S | p.Ser384Ser |
| 165087 | C | 3.33 | 5.24E−08 | 0 | 0.8871 | 0.4085 | BARF1 | S | p.Cys14Cys |
| 146558 | T | 3.31 | 6.45E−08 | 0.0416667 | 0.8871 | 0.4225 | | | |
| 147682 | G | 3.29 | 7.32E−08 | 0 | 0.8871 | 0.4225 | | | |
| 158778 | C | 3.24 | 2.65E−06 | 0.123711 | 0.91935 | 0.5141 | BALF4 | S | p.Ala29Ala |
| 127598 | A | 3.14 | 8.98E−07 | 0.583333 | 0.90323 | 0.4789 | BTRF1 | S | p.Leu82Leu |
| 127616 | G | 3.14 | 8.98E−07 | 0.729167 | 0.90323 | 0.4789 | BTRF1 | S | p.Arg88Arg |
| 147103 | T | 3.14 | 2.19E−07 | 0.0104167 | 0.8871 | 0.4437 | | | |
| 163464 | A | 3.13 | 6.73E−07 | 0 | 0.871 | 0.4085 | BALF2 | S | p.Ser283Ser |
| 148489 | T | 3.08 | 9.45E−08 | 0 | 0.871 | 0.4085 | | | |
| 127198 | T | 3.03 | 2.09E−06 | 0.03125 | 0.90323 | 0.507 | BcRF1 | S | p.Val674Val |
| 157806 | T | 3.02 | 2.18E−06 | 0.257732 | 0.90323 | 0.5 | BALF4 | S | p.Glu353Glu |
| 126226 | A | 3.00 | 5.91E−08 | 0.0104167 | 0.8548 | 0.3873 | BcRF1 | S | p.Ala350Ala |
| 127466 | C | 2.99 | 2.86E−06 | 0.822917 | 0.90323 | 0.5141 | BTRF1 | S | p.His38His |
| 146628 | T | 2.98 | 2.16E−07 | 0 | 0.871 | 0.4296 | | | |

TABLE 2-continued

SNPs assigned to PC1 pass genome-wide significance cut-off under logistic regression model

| Coordinate | Risk allele | Odd ratio | P in logistic regression | Frequency in non-endemic origins | Frequency in NPC | Frequency in Control | Gene | Nonsynonymous (N)/ synonymous (S) | Annotation |
|---|---|---|---|---|---|---|---|---|---|
| 127841 | A | 2.97 | 3.35E−06 | 0.03125 | 0.90323 | 0.5211 | BTRF1 | S | p.Glu163Glu |
| 128037 | A | 2.97 | 3.35E−06 | 0.0729167 | 0.90323 | 0.5211 | BTRF1 | N | p.Thr229Ala |
| 128269 | A | 2.97 | 3.35E−06 | 0.21875 | 0.90323 | 0.5211 | BTRF1 | N | p.Pro306Gln |
| 112981 | T | 2.80 | 3.39E−07 | 0 | 0.8548 | 0.4155 | BDRF1 | N | p.Gln111Leu |
| 130688 | A | 2.76 | 1.37E−05 | 0.0729167 | 0.90323 | 0.5423 | BXLF2 | S | p.Leu20Leu |
| 121384 | T | 2.74 | 1.28E−07 | 0 | 0.8226 | 0.3732 | BcLF1 | S | p.Pro1265Pro |
| 127992 | A | 2.63 | 1.67E−06 | 0.0104167 | 0.8548 | 0.4437 | BTRF1 | N | p.Ala214Thr |
| 108207 | C | 2.63 | 3.51E−07 | 0 | 0.8226 | 0.3803 | | | |
| 117995 | T | 2.63 | 6.93E−07 | 0 | 0.8387 | 0.4085 | BDRF1 | S | p.Leu669Leu |
| 163926 | T | 2.52 | 1.14E−06 | 0 | 0.8226 | 0.4014 | BALF2 | S | p.Arg129Arg |
| 120361 | T | 2.50 | 2.73E−06 | 0 | 0.8387 | 0.4366 | BDLF1 | S | p.Ala219Ala |
| 118350 | T | 2.47 | 7.48E−06 | 0 | 0.8548 | 0.4718 | BDLF3 | S | p.Thr143Thr |
| 118433 | A | 2.47 | 7.48E−06 | 0 | 0.8548 | 0.4718 | BDLF3 | N | p.Ala116Ser |
| 122141 | G | 0.38 | 2.16E−07 | 0 | 0.8065 | 0.3662 | BcLF1 | N | p.Val1013Ala |

REFERENCES

1. Knipe D M, Howley P M, Griffin D E, Lamb R A, Martin M A, Roizman B, Straus S E. Field's Virologyed: Lippincott Williams & Wilkins 2007.
2. Swaminathan S. Noncoding RNAs produced by oncogenic human herpesviruses. J Cell Physiol 2008; 216:321-6.
3. Chang C M, Yu K J, Mbulaiteye S M, Hildesheim A, Bhatia K. The extent of genetic diversity of Epstein-Barr virus and its geographic and disease patterns: a need for reappraisal. Virus Res 2009; 143:209-21.
4. Burrows J M, Khanna R, Sculley T B, Alpers M P, Moss D J, Burrows S R. Identification of a naturally occurring recombinant Epstein-Barr virus isolate from New Guinea that encodes both type 1 and type 2 nuclear antigen sequences. J Virol 1996; 70:4829-33.
5. Palser A L, Grayson N E, White R E, Corton C, Correia S, Ba abdullah M M, Watson S J, Cotten M, Arrand J R, Murray P G, Allday M J, Rickinson A B, et al. Genome Diversity of Epstein-Barr Virus from Multiple Tumor Types and Normal Infection. J Virol 2015; 89:5222-37.
6. Grunewald V, Bonnet M, Boutin S, Yip T, Louzir H, Levrero M, Seigneurin J M, Raphael M, Touitou R, Martel-Renoir D, Cochet C, Durandy A, et al. Amino-acid change in the Epstein-Barr-virus ZEBRA protein in undifferentiated nasopharyngeal carcinomas from Europe and North Africa. International journal of cancer 1998; 75:497-503.
7. Sacaze C, Henry S, Icart J, Mariame B. Tissue specific distribution of Epstein-Barr virus (EBV) BZLF1 gene variants in nasopharyngeal carcinoma (NPC) bearing patients. Virus Res 2001; 81:133-42.
8. Dardari R, Khyatti M, Cordeiro P, Odda M, ElGueddari B, Hassar M, Menezes J. High frequency of latent membrane protein-1 30-bp deletion variant with specific single mutations in Epstein-Barr virus-associated nasopharyngeal carcinoma in Moroccan patients. International journal of cancer 2006; 118:1977-83.
9. See H S, Yap Y Y, Yip W K, Seow H F. Epstein-Barr virus latent membrane protein-1 (LMP-1) 30-bp deletion and Xho I-loss is associated with type III nasopharyngeal carcinoma in Malaysia. World J Surg Oncol 2008; 6:18.
10. Zhang X S, Wang H H, Hu L F, Li A, Zhang R H, Mai H Q, Xia J C, Chen L Z, Zeng Y X. V-val subtype of Epstein-Barr virus nuclear antigen 1 preferentially exists in biopsies of nasopharyngeal carcinoma. Cancer Letters 2004; 211:11-18.
11. Cheung S T, Leung S F, Lo K W, Chiu K W, Tam J S, Fok T F, Johnson P J, Lee J C, Huang D P. Specific latent membrane protein 1 gene sequences in type 1 and type 2 Epstein-Barr virus from nasopharyngeal carcinoma in Hong Kong. International journal of cancer 1998; 76:399-406.
12. Bolger A M, Lohse M, Usadel B. Trimmomatic: a flexible trimmer for Illumina sequence data. Bioinformatics 2014; 30:2114-20.
13. Bankevich A, Nurk S, Antipov D, Gurevich A A, Dvorkin M, Kulikov A S, Lesin V M, Nikolenko S I, Pham S, Prjibelski A D, Pyshkin A V, Sirotkin A V, et al. SPAdes: A New Genome Assembly Algorithm and Its Applications to Single-Cell Sequencing. Journal of Computational Biology 2012; 19:455-77.
14. Li H. Minimap2: pairwise alignment for nucleotide sequences. Bioinformatics 2018.
15. Assefa S, Keane T M, Otto T D, Newbold C, Berriman M. ABACAS: algorithm-based automatic contiguation of assembled sequences. Bioinformatics 2009; 25:1968-69.
16. Boetzer M, Pirovano W. Toward almost closed genomes with GapFiller. Genome Biology 2012; 13.
17. Kurtz S, Phillippy A, Delcher A L, Smoot M, Shumway M, Antonescu C, Salzberg S L. Versatile and open software for comparing large genomes. Genome Biology 2004; 5:R12.
18. Li H. Aligning sequence reads, clone sequences and assembly contigs with BWA-MEM. arXiv preprint arXiv: 1303.3997 2013.
19. Li H. A statistical framework for SNP calling, mutation discovery, association mapping and population genetical parameter estimation from sequencing data. Bioinformatics 2011; 27:2987-93.
20. Barrett J C, Fry B, Mailer J, Daly M J. Haploview: analysis and visualization of L D and haplotype maps. Bioinformatics 2004; 21:263-65.
21. Chang C C, Chow C C, Tellier L C A M, Vattikuti S, Purcell S M, Lee J J. Second-generation PLINK: rising to the challenge of larger and richer datasets. GigaScience 2015; 4.
22. Kolde R. Pheatmap: pretty heatmaps. R package version 2012; 61.

23. Danecek P, Auton A, Abecasis G, Albers C A, Banks E, DePristo M A, Handsaker R E, Lunter G, Marth G T, Sherry S T, McVean G, Durbin R. The variant call format and VCFtools. *Bioinformatics* 2011; 27:2156-58.
24. Corander J, Marttinen P. Bayesian identification of admixture events using multilocus molecular markers. *Molecular Ecology* 2006; 15:2833-43.
25. Francis R M. Pophelper: an R package and web app to analyse and visualize population structure. *Molecular Ecology* Resources 2017; 17:27-32.
26. Paradis E, Claude J, Strimmer K. APE: Analyses of Phylogenetics and Evolution in R language. *Bioinformatics* 2004; 20:289-90.
27. Capella-Gutierrez S, Silla-Martinez J M, Gabaldon T. TrimAl: a tool for automated alignment trimming in large-scale phylogenetic analyses. *Bioinformatics* 2009; 25:1972-73.
28. Nguyen L T, Schmidt H A, von Haeseler A, Minh B Q. IQ-TREE: A Fast and Effective Stochastic Algorithm for Estimating Maximum-Likelihood Phylogenies. *Molecular Biology and Evolution* 2015; 32:268-74.
29. Yu G, Smith D K, Zhu H, Guan Y, Lam T T Y, McInerny G. Ggtree: anrpackage for visualization and annotation of phylogenetic trees with their covariates and other associated data. *Methods in Ecology and Evolution* 2017; 8:28-36.
30. Earle S G, Wu C H, Charlesworth J, Stoesser N, Gordon N C, Walker T M, Spencer C C A, Iqbal Z, Clifton D A, Hopkins K L, Woodford N, Smith E G, et al. Identifying lineage effects when controlling for population structure improves power in bacterial association studies. *Nature Microbiology* 2016; 1.
31. Browning Brian L, Browning Sharon R. Genotype Imputation with Millions of Reference Samples. *The American Journal of Human Genetics* 2016; 98:116-26.
32. Zhou X, Stephens M. Genome-wide efficient mixed-model analysis for association studies. *Nature Genetics* 2012; 44:821-24.
33. Aulchenko Y S, Ripke S, Isaacs A, van Duijn C M. GenABEL: an R library for genome-wide association analysis. *Bioinformatics* 2007; 23:1294-96.
34. Reuter J S, Mathews D H. RNAstructure: software for RNA secondary structure prediction and analysis. BMC *Bioinformatics* 2010; 11.
35. Kwok H, Wu C W, Palser A L, Kellam P, Sham P C, Kwong D L, Chiang A K. Genomic diversity of Epstein-Barr virus genomes isolated from primary nasopharyngeal carcinoma biopsy samples. *J Virol* 2014; 88:10662-72.
36. Kim S M, Kang S H, Lee W K. Identification of two types of naturally-occurring intertypic recombinants of Epstein-Barr virus. *Mol Cells* 2006; 21:302-07.
37. Dawson C W, Port R J, Young L S. The role of the EBV-encoded latent membrane proteins LMP1 and LMP2 in the pathogenesis of nasopharyngeal carcinoma (NPC). *Seminars in Cancer Biology* 2012; 22:144-53.
38. Miller W E, Edwards R H, Walling D M, Raab-Traub N. Sequence variation in the Epstein—Barr virus latent membrane protein 1. *Journal of General Virology* 1994; 75:2729-40.
39. Zhang X S, Song K H, Mai H Q, Jia W H, Feng B J, Xia J C, Zhang R H, Huang L X, Yu X J, Feng Q S, Huang P, Chen J J, et al. The 30-bp deletion variant: a polymorphism of latent membrane protein 1 prevalent in endemic and non-endemic areas of nasopharyngeal carcinomas in China. *Cancer Letters* 2002; 176:65-73.
40. Power R A, Parkhill J, de Oliveira T. Microbial genome-wide association studies: lessons from human GWAS. *Nature Reviews Genetics* 2016; 18:41-50.
41. Shen Z-c, Luo B, Chen J-n, Chao Y, Shao C-k, Liu Q-q, Wang Y. High Prevalence of the EBER Variant EB-8m in Endemic Nasopharyngeal Carcinomas. *PLOS ONE* 2015; 10:e0121420.
42. Feng F T, Cui Q, Liu W S, Guo Y M, Feng Q S, Chen L Z, Xu M, Luo B, Li D J, Hu L F, Middeldorp J M, Ramayanti O, et al. A single nucleotide polymorphism in the Epstein-Barr virus genome is strongly associated with a high risk of nasopharyngeal carcinoma. *Chinese Journal of Cancer* 2015; 34.
43. Tong J H M, Lo K W, Au F W L, Huang D P, To K F. Re: Discrete Alterations in the BZLF1 Promoter in Tumor and Non-Tumor-Associated Epstein-Barr Virus. *JNCI Journal of the National Cancer Institute* 2003; 95:1008-09.
44. Lee N, Moss Walter N, Yario Therese A, Steitz Joan A. EBV Noncoding RNA Binds Nascent RNA to Drive Host PAX5 to Viral DNA. *Cell* 2015; 160:607-18.
45. Iwakiri D, Sheen T S, Chen J Y, Huang D P, Takada K. Epstein-Barr virus-encoded small RNA induces insulin-like growth factor 1 and supports growth of nasopharyngeal carcinoma-derived cell lines. *Oncogene* 2004; 24:1767.
46. Samanta M, Iwakiri D, Kanda T, Imaizumi T, Takada K. E B virus-encoded RNAs are recognized by RIG-I and activate signaling to induce type I IFN. *The EMBO Journal* 2006; 25:4207-14.
47. Iwakiri D, Zhou L, Samanta M, Matsumoto M, Ebihara T, Seya T, Imai S, Fujieda M, Kawa K, Takada K. Epstein-Barr virus (EBV)-encoded small RNA is released from EBV-infected cells and activates signaling from toll-like receptor 3. *The Journal of Experimental Medicine* 2009; 206:2091-99.
48. Herbert K M, Pimienta G. Consideration of Epstein-Barr Virus-Encoded Noncoding RNAs EBER1 and EBER2 as a Functional Backup of Viral Oncoprotein Latent Membrane Protein 1. *mBio* 2016; 7.
49. Chen P E, Shapiro B J. The advent of genome-wide association studies for bacteria. *Current Opinion in Microbiology* 2015; 25:17-24.
50. Tse K P, Su W H, Chang K P, Tsang N M, Yu C J, Tang P, See L C, Hsueh C, Yang M L, Hao S P, Li H Y, Wang M H, et al. Genome-wide Association Study Reveals Multiple Nasopharyngeal Carcinoma-Associated Loci within the HLA Region at Chromosome 6p21.3. *The American Journal of Human Genetics* 2009; 85:194-203.
51. Bei J X, Li Y, Jia W H, Feng B J, Zhou G, Chen L Z, Feng Q S, Low H Q, Zhang H, He F, Tai E S, Kang T, et al. A genome-wide association study of nasopharyngeal carcinoma identifies three new susceptibility loci. *Nature Genetics* 2010; 42:599-603.
52. Dai W, Zheng H, Cheung A K L, Tang C S-m, Ko J M Y, Wong B W Y, Leong M M L, Sham P C, Cheung F, Kwong D L W, Ngan R K C, Ng W T, et al. Whole-exome sequencing identifiesMST1Ras a genetic susceptibility gene in nasopharyngeal carcinoma. *Proceedings of the National Academy of Sciences* 2016; 113:3317-22.
53. Li Y Y, Chung G T Y, Lui V W Y, To K F, Ma B B Y, Chow C, Woo J K S, Yip K Y, Seo J, Hui E P, Mak M K F, Rusan M, et al. Exome and genome sequencing of nasopharynx cancer identifies NF-κB pathway activating mutations. *Nature communications* 2017; 8.

What is claimed is:

1. A method comprising:
    (i) performing an assay to determine polynucleotide sequence of at least a portion of Epstein Barr virus (EBV) genomic sequence present in a biological sample taken from an individual without clinical symptoms of nasopharyngeal carcinoma; and
    (ii) detecting alleles 5399A, 5850T, 6484T, 6584G, 7125G, 7134C, 7187A, 7198T, 7206A, 7213C, 7233A, 7262A, 7297T, 7327C, and 8568T in the at least a portion of EBV genomic sequence.

2. The method of claim 1, further comprising, prior to step (i), a step of isolating DNA from the sample.

3. The method of claim 1, further comprising, prior to step (i), a step of performing an amplification reaction to amplify the at least a portion of EBV genomic sequence.

4. The method of claim 3, wherein the amplification reaction is a polymerase chain reaction (PCR).

5. The method of claim 1, wherein the sample is a saliva sample.

6. The method of claim 1, wherein the assay in step (i) comprises a sequencing assay.

7. The method of claim 1, wherein at least one additional risk allele 137316C, 59515CCTCCTT, or 59518CCTCCTA is detected in step (ii).

8. The method of claim 1, wherein two or more additional risk alleles selected from 137316C, 59515CCTCCTT, and 59518CCTCCTA are detected in step (ii).

9. The method of claim 1, wherein the individual resides in South East Asia.

10. The method of claim 9, wherein the individual resides in Hong Kong or the Guangdong Province of China.

* * * * *